# United States Patent [19]

Hinnen et al.

[11] Patent Number: 5,436,136
[45] Date of Patent: Jul. 25, 1995

[54] REPRESSIBLE YEAST PROMOTERS

[75] Inventors: Albert Hinnen, Basel; Bernd Meyhack, Magden, both of Switzerland

[73] Assignee: Ciba-Geigy Corporation, Ardsley, N.Y.

[21] Appl. No.: 811,898

[22] Filed: Dec. 20, 1991

Related U.S. Application Data

[63] Continuation of Ser. No. 637,994, Jan. 3, 1991, abandoned, which is a continuation of Ser. No. 900,871, Aug. 27, 1986, abandoned.

[30] Foreign Application Priority Data

Aug. 29, 1985 [GB]  United Kingdom ............... 8521496

[51] Int. Cl.$^6$ ............... C12N 1/19; C12N 15/11; C12N 15/63; C12N 15/81
[52] U.S. Cl. ............... 435/69.1; 435/172.3; 435/320.1; 435/254.2; 536/24.1; 935/37; 935/28
[58] Field of Search ............... 435/69.1, 69.6, 172.1, 435/172.3, 255, 320.1, 942, 254.2; 536/27, 24.1; 935/28, 37, 36

[56] References Cited

U.S. PATENT DOCUMENTS 4,876,197  10/1989  Burke et al. .................. 435/172.3

FOREIGN PATENT DOCUMENTS

| 103409 | 7/1982 | European Pat. Off. . |
| 0100561 | 3/1984 | European Pat. Off. . |
| 123544 | 10/1984 | European Pat. Off. . |
| 164556 | 5/1985 | European Pat. Off. . |
| 0143081 | 4/1986 | European Pat. Off. . |
| WO84/4757 | 2/1984 | WIPO . |

OTHER PUBLICATIONS

Janice P. Holland et al., The Journal of Biological Chemistry 254(19):9639–9645 (1979).
L. Guarente, Cell 36, 799–800 (1984).
L. Guarente et al., Proc. Natl. Acad. Sci. USA 79, 7410–7414 (1982).
L. Guarente et al., Cell 36, 503–511 (1984).
Tolstoshev, P et al Chemical Abstracts vol. 104 Abstract No. 163014n (1986).
Rink et al Nucl. Acids Res vol. 12 pp. 6369–6387 (1984).
Holland, J. P et al J. Biol. Chem vol. 255 pp. 2596–2605 (1980).

Primary Examiner—Robert W. Wax
Assistant Examiner—D. C. Jacobson
Attorney, Agent, or Firm—JoAnn Villamizar

[57]  ABSTRACT

Novel upstream activation sites of the yeast PHO5 gene are used to produce inducible yeast hybrid promoters. The yeast hybrid promoters can be used to control transcription of a polypeptide coding region foreign to yeast in a yeast expression vector.

29 Claims, 10 Drawing Sheets

Fig. 1: DNA SEQUENCE OF THE BamHI-SalI RESTRICTION FRAGMENT OF PHO5 INCLUDING THE PHO5 PROMOTER REGION

```
                                                            BamHI
                                                              ↓
                                                              GG
-540       -530       -520       -510       -500
  ATCCGAAAGT TGTATTCAAC AAGAATGCGC AAATATGTCA ACGTATTTGG
-490       -480       -470       -460       -450
  AAGTCATCTT ATGTGCGCTG CTTTAATGTT TTCTCATGTA AGCGGACGTC
-440       -430       -420       -410       -400
  GTCTATAAAC TTCAAACGAA GGTAAAAGGT TCATAGCGCT TTTTCTTTGT
-390       -380       -370       -360       -350
  CTGCACAAAG AAATATATAT TAAATTAGCA CGTTTTCGCA TAGAACGCAA
-340       -330       -320       -310       -300
  CTGCACAATG CCAAAAAAAG TAAAAGTGAT TAAAAGAGTT AATTGAATAG
-290       -280  ClaI -270       -260       -250
                   ↓
  GCAATCTCTA AATGAATCGA TACAACCTTG GCACTCACAC GTGGGACTAG
-240       -230       -220       -210       -200
  CACAGACTAA ATTTATGATT CTGGTCCCTG TTTTCGAAGA GATCGCACAT
-190       -180 BstEII-170       -160       -150
                    ↓
  GCCAAATTAT CAAATTGGTC ACCTTACTTG GCAAGGCATA TACCCATTTG
-140       -130       -120       -110       -100
  GGATAAGGGT AAACATCTTT GAATTGTCGA AATGAAACGT ATATAAGCGC
-90        -80        -70        -60        -50
  TGATGTTTTG CTAAGTCGAG GTTAGTATGG CTTCATCTCT CATGAGAATA
-40        -30        -20        -10        -1         10
  AGAACAACAA CAAATAGAGC AAGCAAATTC GAGATTACCA ATGTTTAAAT
              20         30         40         50         60
  CTGTTGTTTA TTCAATTTTA GCCGCTTCTT TGGCCAATGC AGGTACCATT
              70         80  SalI
                               ↓
  CCCTTAGGCA AACTAGCCGA TGTCGAC
```

Fig. 2: THE PROMOTER REGION OF THE GAPDH GENE

```
TaqI    -670        -660        -650        -640
 ↓
 TCGAGT TTATCATTAT CAATACTCGC CATTTCAAAG AATACGTAAA
-630        -620        -610        -600        -590
 TAATTAATAG TAGTGATTTT CCTAACTTTA TTTAGTCAAA AAATTAGCCT
-580        -570        -560        -550        -540
 TTTAATTCTG CTGTAACCCG TACATGCCAA AATAGGGGGC GGGTTACACA
-530        -520        -510        -500        -490
 GAATATATAA CACTGATGGT GCTTGGGTGA ACAGGTTTAT TCCTGGCATC
-480        -470        -460        -450        -440
 CACTAAATAT AATGGAGCCC GCTTTTTAAG CTGGCATCCA GAAAAAAAAA
-430        -420        -410        -400        -390
 GAATCCCAGC ACCAAAATAT TGTTTTCTTC ACCAACCATC AGTTCATAGG
-380        -370        -360        -350        -340
 TCCATTCTCT TAGCGCAACT ACAGAGAACA GGGCACAAAC AGGCAAAAAA
-330        -320        -310        -300        -290
 CGGGCACAAC CTCAATGGAG TGATGCAACC TGCCTGGAGT AAATGATGAC
-280        -270        -260        -250        -240
 ACAAGGCAAT TGACCCACGC ATGTATCTAT CTCATTTTCT TACACCTTCT
-230        -220        -210        -200        -190
 ATTACCTTCT GCTCTCTCTG ATTTGGAAAA AGCTGAAAAA AAAGGTTGAA
-180        -170        -160        -150        -140
 ACCAGTTCCC TGAAATTATT CCCCTACTTG ACTAATAAGT ATATAAAGAC
-130        -120        -110        -100        -90
 GGTAGGTATT GATTGTAATT CTGTAAATCT ATTTCTTAAA CTTCTTAAAT
-80         -70         -60         -50 DraI   -40
                                              ↓
 TCTACTTTTA TAGTTAGTCT TTTTTTTAGT TTTAAACAC CAAGAACTTA
-30 TaqI    -20         -10         -1
    ↓
 GTTTCGAATA AACACACATA AATAAACAAA ATG
```

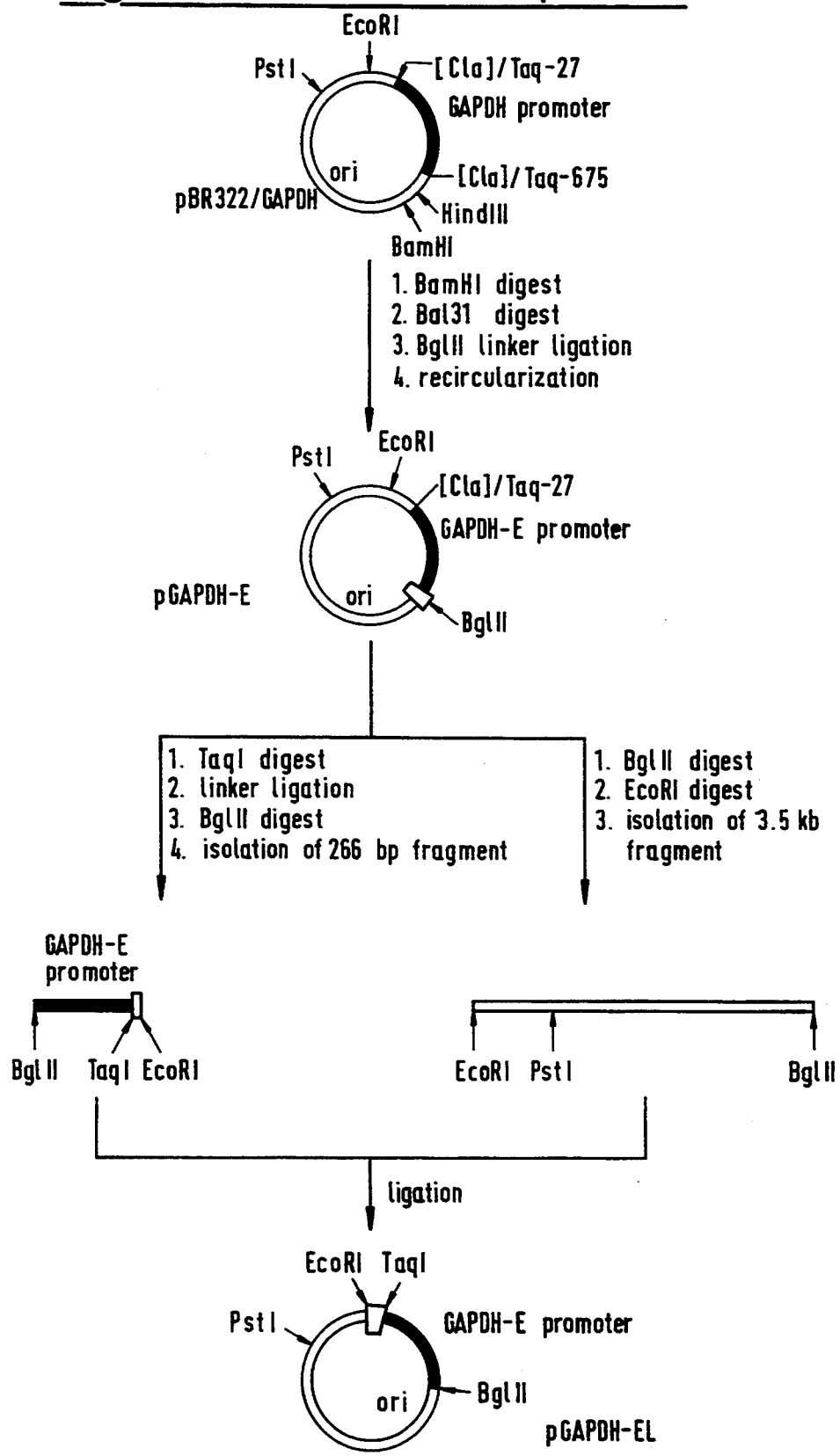

Fig. 4: SEQUENCE OF BglII-EcoRI FRAGMENTS FROM PLASMIDS pGAPDH-FL AND pGAPDH-EL, RESPECTIVELY, COMPRISING PART OF THE GAPDH PROMOTER a. pGAPDH-FL

```
                        5'-GATC TGCTGAAAAA AAAGGTTGAA
ACCAGTTCCC TGAAATTATT CCCCTACTTG ACTAATAAGT ATATAAAGAC
GGTAGGTATT GATTGTAATT CTGTAAATCT ATTTCTTAAA CTTCTTAAAT
TCTACTTTTA TAGTTAGTCT TTTTTTTAGT TTTAAAACAC CAAGAACTTA
GTTTCGAATA AACACACATA AATAAAG-3'
``` b. pGAPDH-EL

```
       5'-GATCTGCGC  ATGTATCTAT CTCATTTTCT TACACCTTCT
ATTACCTTCT GCTCTCTCTG ATTTGGAAAA AGCTGAAAAA AAAGGTTGAA
ACCAGTTCCC TGAAATTATT CCCCTACTTG ACTAATAAGT ATATAAAGAC
GGTAGGTATT GATTGTAATT CTGTAAATCT ATTTCTTAAA CTTCTTAAAT
TCTACTTTTA TAGTTAGTCT TTTTTTTAGT TTTAAAACAC CAAGAACTTA
GTTTCGAATA AACACACATA AATAAAG-3'
```

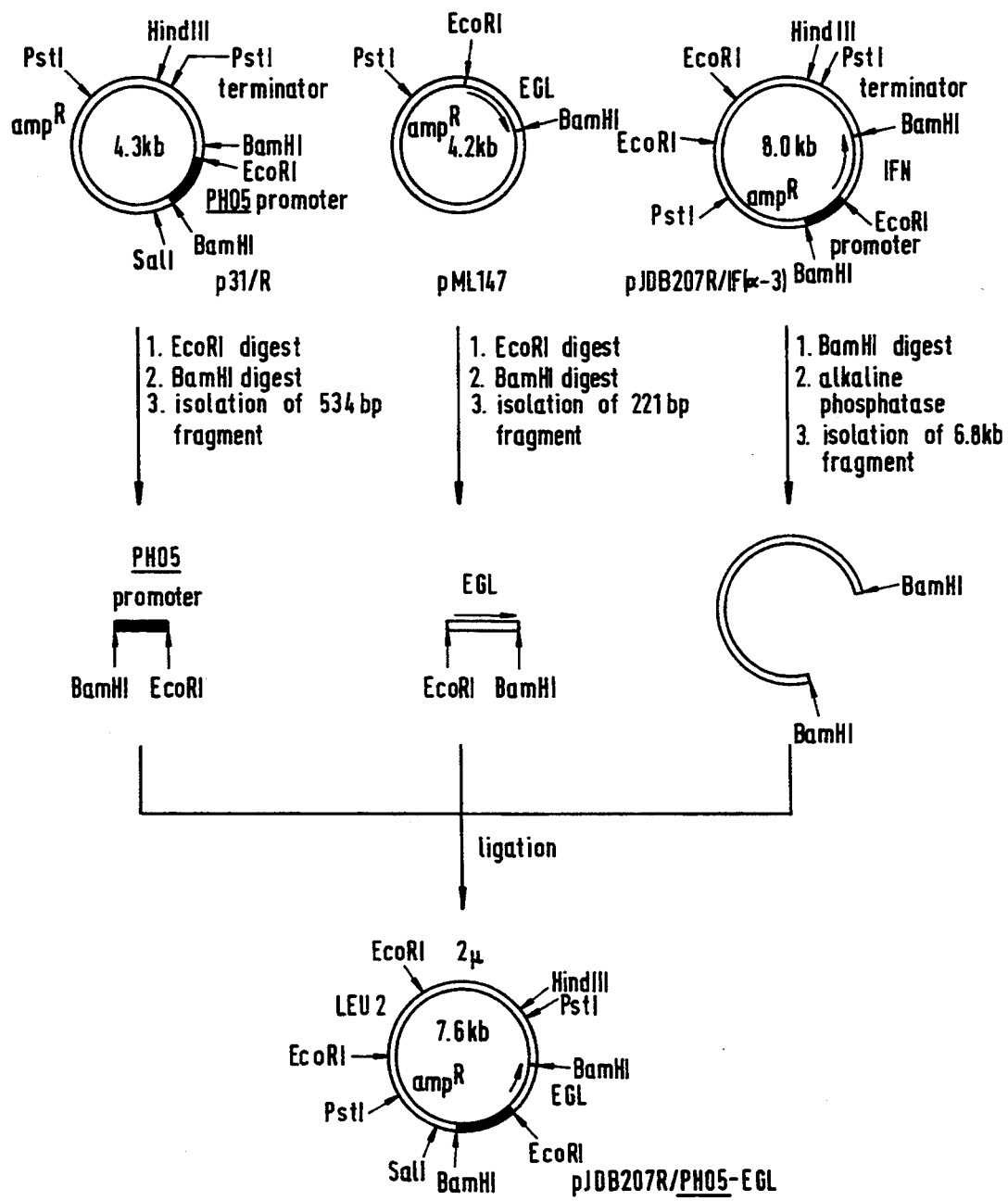

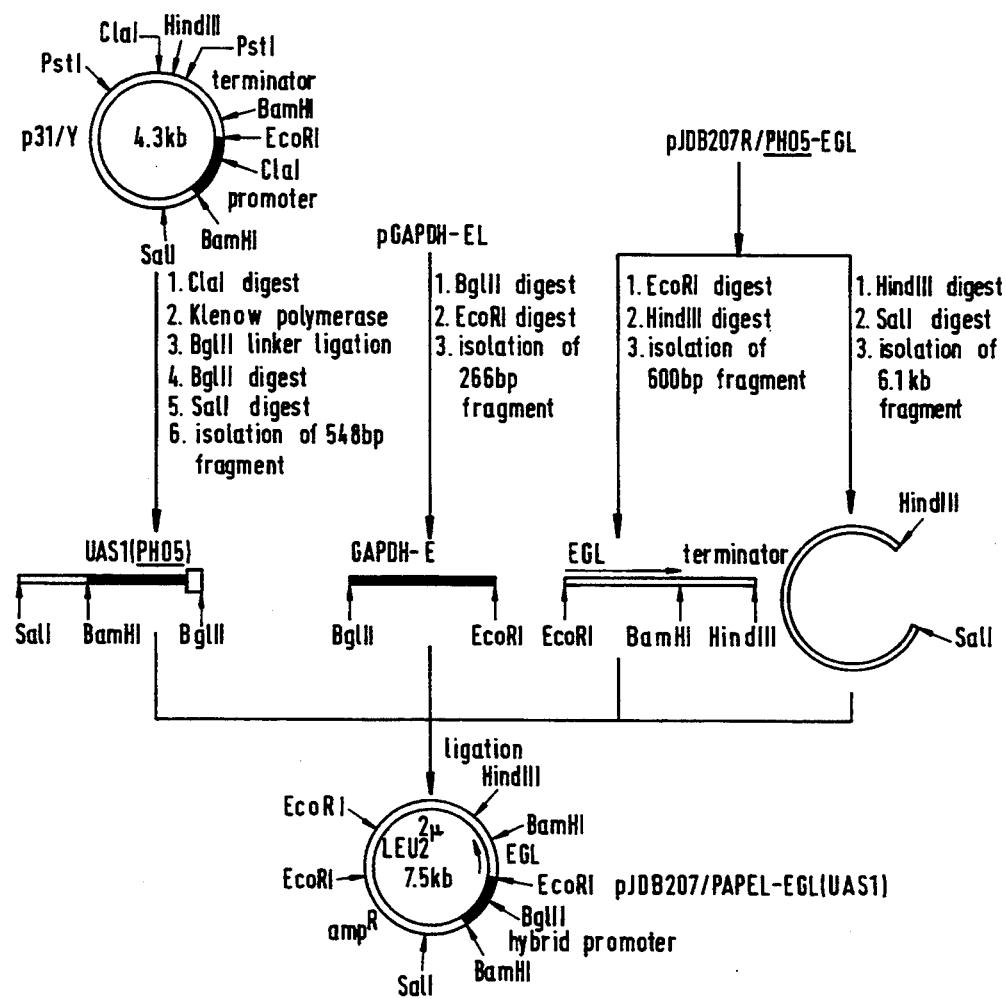
Fig.6: CONSTRUCTION OF PLASMID pJDB207/PAPEL-EGL(UAS1) COMPRISING A HYBRID PHO5/GAPDH PROMOTER

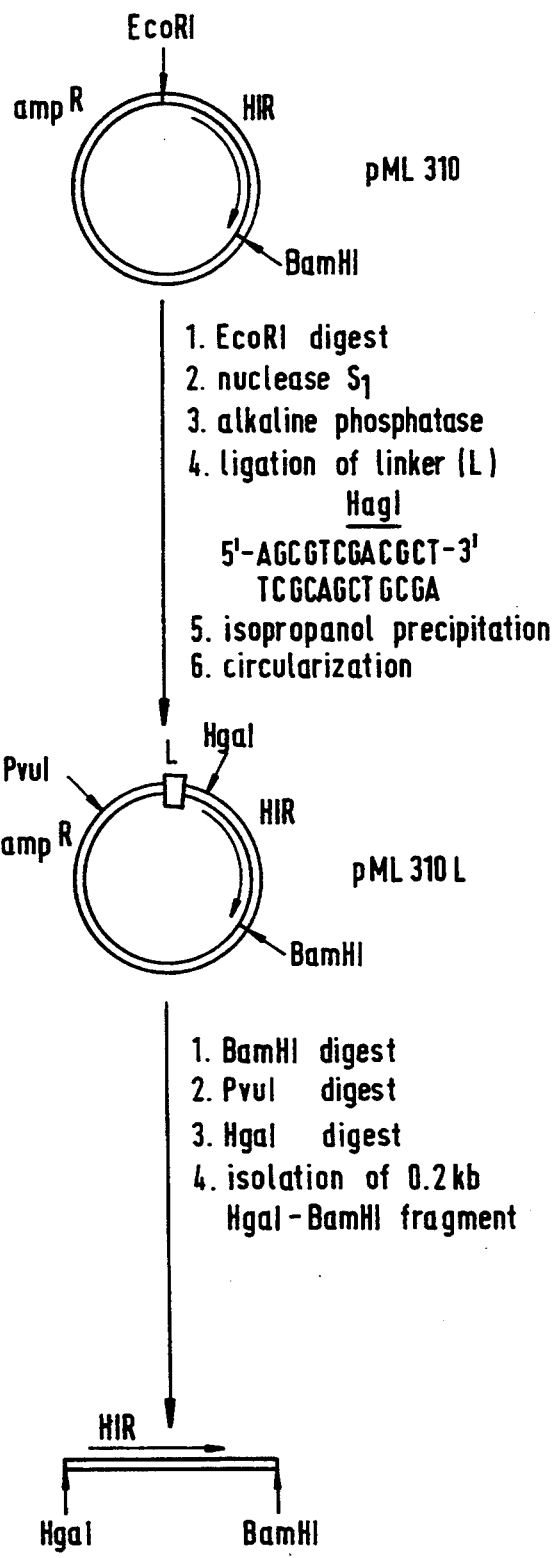

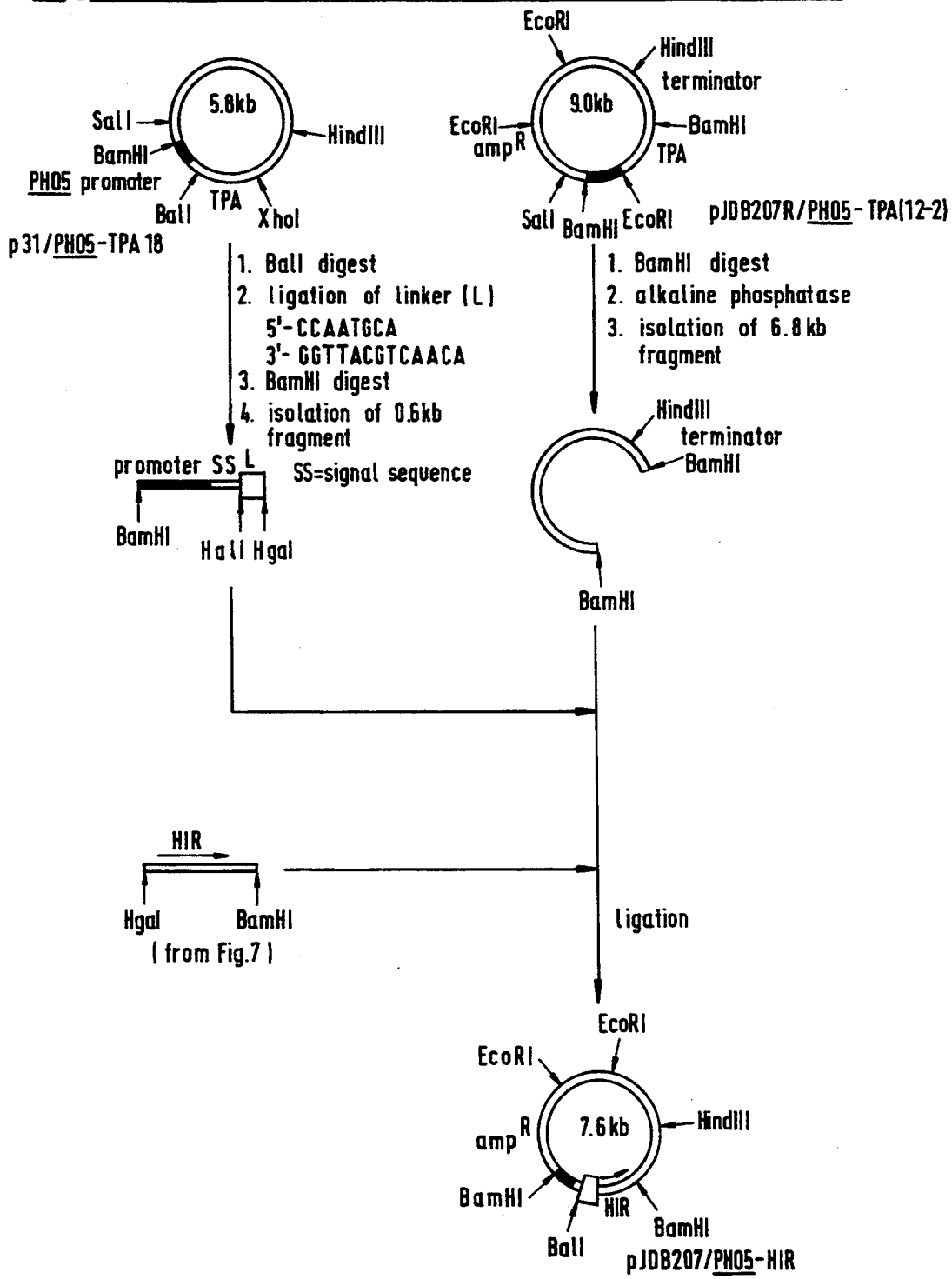
Fig. 8: CONSTRUCTION OF EXPRESSION PLASMID pJDB207/PHO5-HIR

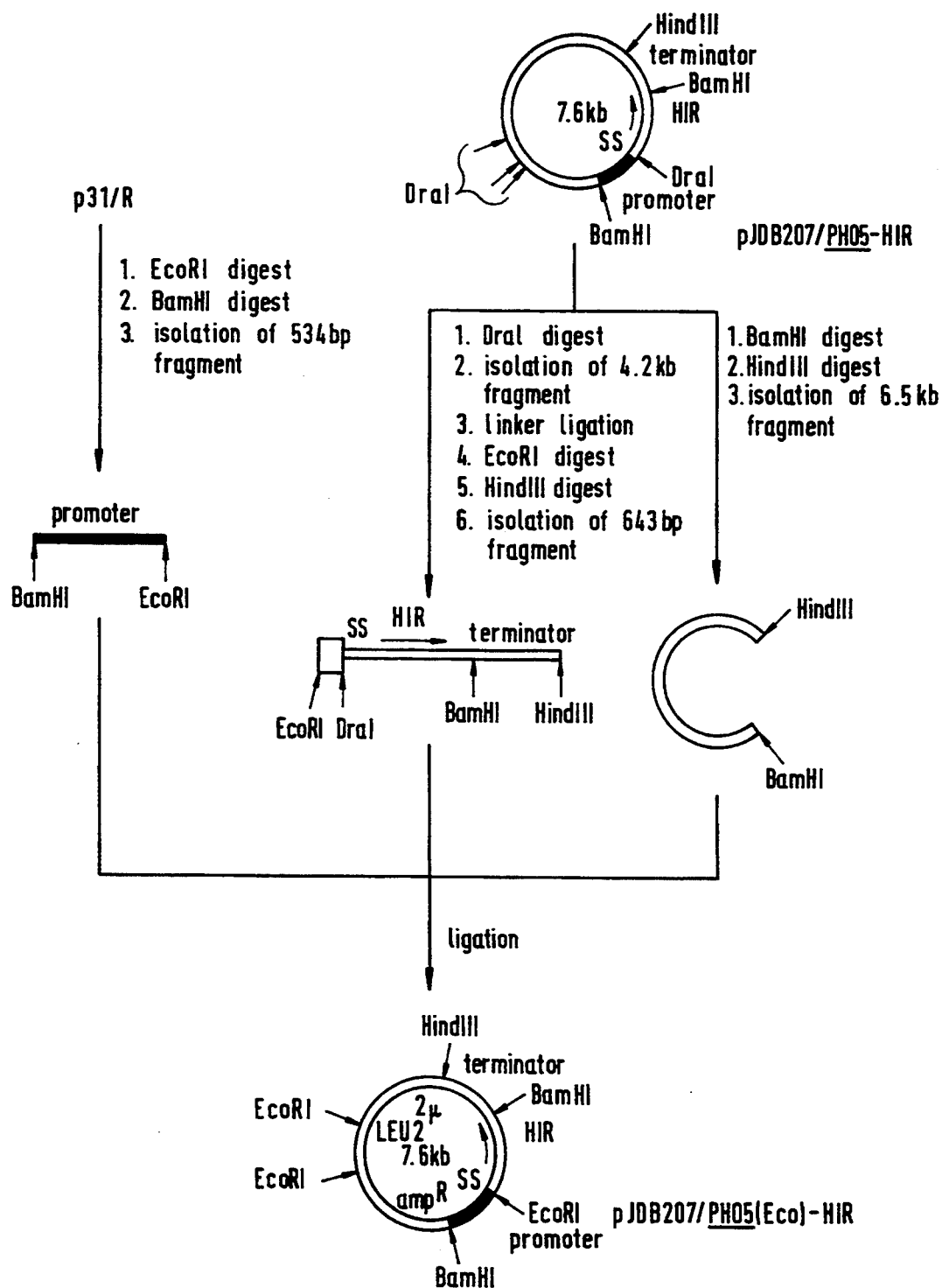
Fig.9: CONSTRUCTION OF PLASMID pJDB207/PHO5(Eco)-HIR

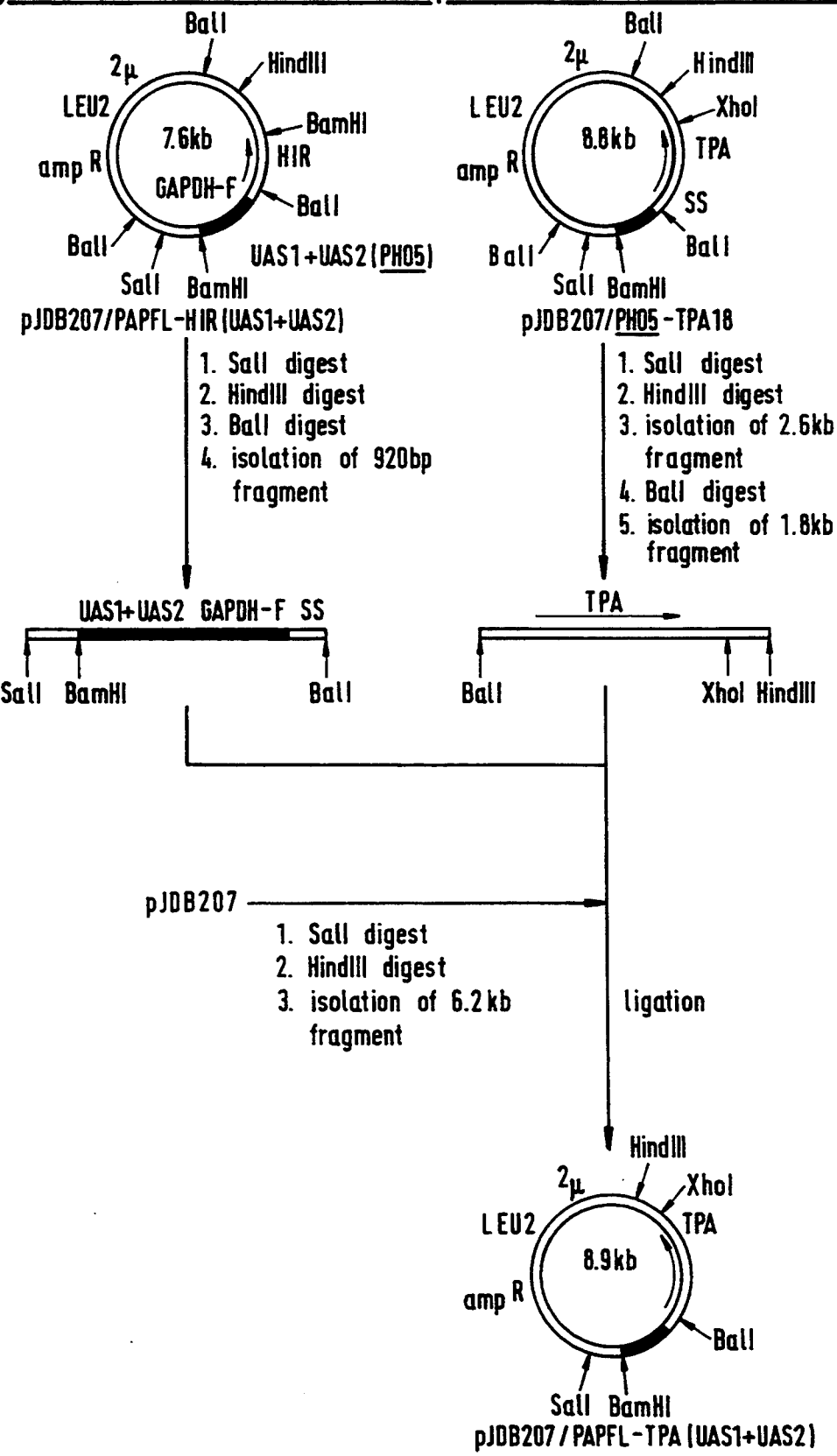

5,436,136

REPRESSIBLE YEAST PROMOTERS

This application is a continuation of application Ser. No. 637,994, filed Jan. 3, 1991, which is a continuation of application Ser. No. 900,71, filed Aug. 27, 1986 both abandoned.

FIELD OF THE INVENTION

The invention relates to the production of foreign polypeptides in yeast hosts using recombinant DNA techniques, More specifically, the invention relates to novel upstream activation sequences, to hybrid yeast promoters comprising such upstream activation sequences, to novel hybrid vectors useful for the transformation of yeast cells, to such transformed yeast cells and to the use of such transformed yeast cells for the production of polypeptides foreign to yeast.

BACKGROUND OF THE INVENTION

During the last years, there was great progress in the field of genetic engineering, and some systems using genetically manipulated microorganisms, especially strains of the enterobacterium *Escherichia coli* and of baker's yeast (*Saccharomyces cerevisiae*), are now working. However, there exists a need for additional and improved systems, especially eukaryotic systems, such as yeasts, which are suitable for the economic and large-scale production of proteins in industry. At present, various yeast vectors are available for gene cloning. For the efficient expression of foreign genes in yeast structural coding sequences will have to be combined with strong yeast promoters which, advantageously, should show regulatory features which allow exogenous control of gene expression. Since efficiency of expression (product formation) is believed to be a function of and proportional to the strength of the promoter employed, workers in the field of genetic engineering pay special attention to the development of powerful promoter systems.

In vitro mutagenesis of cloned yeast genes coding for proteins and their reintroduction back into yeast cells for functional analysis have allowed the identification of various essential cis-acting promoter elements [for review see L. Guarente, Cell 36, 799(1984)]. Beginning with the elements immediately flanking the protein coding region at the 5' end of the gene these elements include:

- a 5' transcribed leader region, rather A-T rich, sometimes including a CAACAACAA (or related sequence) motif,
- transcription initiation points, located about 40 to 60 bp (sometimes more) from the translational start codon ATG, usually pointing to a multiplicity of mRNA start sites of different strengths,
- a TATA box (sometimes more than one), located about 40 to 80 bp from the transcription initiation points, presumably acting as essential RNA polymerase II recognition site,
- upstream activation site(s) (UAS), presumptive target sites for regulatory proteins, located about 100 to 300 bp upstream from the TATA box.

The UAS acts in a manner distinct from the regulatory sites found in procaryotes and resemble more the enhancer sites of the mammalian systems. Rather detailed data are available from the yeast GAL 1, GAL 7, GAL 10 cluster where a positively acting regulatory protein (GAL 4 gene product) interacts directly with the UAS of GAL 1–GAL 10 [Giniger et al., Cell 40, 767(1985)].

By fusing promoter segments encoding the UAS of GAL 1–GAL 10 in front of the TATA box of the yeast CYC 1 gene a hybrid promoter was generated whose transcription is now under the control of the UAS of GAL 1–GAL 10, i.e. it is GAL 4 gene dependent [L. Guarente et al., Proc. Natl. Acad. Sci. USA 79, 7410(1984)]. A similar construction was done by fusing promoter elements of CYC 1 and LEU2 [L. Guarente et al. Cell 36, 503(1984)]. Both of these examples include promoter elements and protein coding sequences from yeast and no evidence that these systems work also with genes foreign to yeast is available.

A recently published patent application (PCT 84/4757) describes a UAS element of the yeast PGK gene. The presence of an essential promoter element located between positions $-324$ and $-455$ (from the ATG) is shown. It is alleged that addition of this element in front of other promoters would potentiate the strength of any other yeast promoter. However, no example substantiating this allegation is given, the arguments depending entirely on negative data (destroying a promoter). It is well possible that the element is an essential part of the PGK promoter but it is doubtful whether such an element would work as part of a hybrid promoter. In addition, the UAS of PGK is not associated with a regulatory signal, i.e. it does not allow to control the expression (transcription) of the downstream coding sequence by a specific physiological signal.

Some of the promoters of glycolytic genes are induced in the presence of glucose. They can potentially be turned off if the cells are grown in a glucose-free medium. This means that yeast host cells would have to be transformed and regenerated in a medium where glucose is replaced by other carbon sources (acetate, glycerol, lactate, etc.) in order to protect the cells against a potentially harmful or lethal gene product accumulating within the cells. Since regeneration of protoplasts [A. Hinnen et al. Proc. Natl. Acad. Sci. USA 75, 1929(1978)] or of salt treated whole cells [Ito et al. J. Bacteriol. 153, 163(1983)] is generally done in a rich medium in order to allow rapid regeneration of the cells and formation of colonies, all currently used transformation protocols use glucose as a carbon source. It is expected that regeneration and recovery in a glucose-free medium works very poorly (if at all).

It is generally recognised in the art that the timing of expression must be regulated to ensure that the protein is produced at high levels only when the cell can best tolerate the large amounts of foreign proteins, i.e. outside the growth period. It is also desirable that regulation of expression does not depend on the presence or absence of the most important carbon source for microbial growth, viz. glucose. Regulable and strong promoter systems meeting these requirements for the convenient and technically applicable expression of foreign genes by yeast are scarcely known in the art. There is thus a need for the development of such promoter systems.

Surprisingly it has now been found that combination of the TATA box region of promoters controlling the expression of enzymes involved in the glycolytic pathway and generally believed to belong to the strongest promoters known at present, with upstream promoter elements of a regulable promoter the repression or derepression of which does not depend on the presence or absence of an essential component of the growth medium, such as an essential carbon or nitrogen source, leads to strong hybrid promoters meeting the main requirements imposed on technically applicable promoter systems.

OBJECT OF THE INVENTION

It is an object of the invention to use hybrid promoters, especially promoters of glycolytic genes, brought under the control of the UAS of the acid phosphatase PHO5 gene for the efficient expression of foreign genes in yeast.

The newly isolated UAS signals of the yeast PHO5 gene, hybrid promoters comprising the PHO5 UAS signals, hybrid vectors containing such hybrid promoters and yeast hosts transformed with such hybrid vectors are further objects of the present invention.

Further objects of the invention are methods for the preparation of said UAS signals, said hybrid promoters, said hybrid vectors and said transformed yeast hosts, and the use of said transformed yeast hosts for the production of polypeptides.

DETAILED DESCRIPTION OF THE INVENTION

1. Upstream activation sequences of the yeast acid phosphatase (PHO5) gene and hybrid promoters The invention relates to upstream activation sequences derived from the yeast PHO5 gene and to the use thereof for the production of hybrid promoters.

Prior to the present invention it was not known in the art whether there exist one or more upstream activation sites (or sequences, "UAS") which modulate transcription of the yeast PHO5 gene. The PHO5 gene codes for a repressible yeast acid phosphatase. It is repressed at high concentration of inorganic phosphate and is derepressed under inorganic phosphate starvation [B. Meyhack et al. EMBO-J. 1, 675(1982)].

The analysis of the 5' region of the PHO5 gene has now led to the identification of cis-acting elements that modulate transcription of the PHO5 gene. A 623 bp BamHI-SalI fragment of the 5' region of the PHO5 gene cloned into the phage vector M13mp9 (recombinant vector M13mp9/PHO5 Bam-Sal, see European Patent Application No. 143,081) is digested with exonuclease Ba131 starting from the Bam site and, in another experiment, from the Sal site. Thus, a set of shortened PHO5 promoter fragments are generated which are subjected to sequence analysis and provided with synthetic EcoRI linkers at the shortened ends. By combination of fragments shortened at the Sal site ("left arm promoter fragments") with fragments shortened at the Bam site ("right arm promoter fragments") a set of deletion mutants of the PHO5 promoter region are created which are tested for their ability for effecting expression of the PHO5 structural gene. It was established that deletion between nucleotides $-225$ to $-263$ leads to a fivefold reduction of acid phosphate activity and deletions between nucleotides $-361$ to $-392$ or between nucleotides $-346$ to $-369$ lead to a tenfold reduction of acid phosphatase activity (for numbering of the nucleotides see FIG. 1 of the accompanying drawings). These effects are attributed to upstream activation sites (UAS) which are essential for PHO5 expression. The UAS in the vicinity of nucleotide $-365$ is contained in a 268 bp BamHI-ClaI fragment (nucleotides $-274$ to $-541$) of the 5' region of the PHO5 gene and is designated UAS1(PHO5) whilst an UAS region in the vicinity of nucleotide $-245$ is contained in the 100 bp ClaI-BstEII fragment (nucleotides $-174$ to $-273$) of the 5' region of the PHO5 gene and is designated UAS2(PHO5).

The present invention concerns especially the upstream activation sequences UAS1(PHO5) and UAS2(PHO5) contained in the BamHI-BstEII fragment between nucleotides $-174$ and $-541$ of the PHO5 gene.

The invention concerns furthermore the upstream activation sequence UAS1(PHO5) contained in the BamHI-ClaI fragment between nucleotides $-274$ to $-541$ of the PHO5 gene and the upstream activation sequence UAS2(PHO5) contained in the ClaI-BstEII fragment between nucleotides $-174$ to $-273$ of the PHO5 gene.

Especially preferred is the upstream activation sequence UAS1(PHO5). The exact location of the USA1 regulatory signal within the BamHI-ClaI fragment could be determined. Thus, the UAS1 regulatory signal is contained in a 31 bp DNA fragment (position $-381$ to $-351$ of the PHO5 promoter region). Preferably, the fragment is provided at either side with blunt ended linkers containing suitable restriction sites or with staggered ends specific for a restriction endonuclease, such as EcoRI. The 31 bp fragment has the following sequence:

```
GAAATATATATTAAATTAGCACGTTTTCGCA
CTTTATATATAATTTAATCGTGCAAAAGCGT
```

The process for the preparation of DNA fragments containing the UAS1(PHO5) and/or UAS2(PHO5) sequences comprises cleaving a DNA containing the PHO5 gene, the PHO5 gene or the 5' terminal part thereof with suitable restriction endonucleases and isolating the desired fragments. For example, the 623 bp BamHI-SalI fragment of PHO5 (supra) including the PHO5 promoter and part of the PHO5 coding region is digested with restriction endonucleases BamHI and BstEII and the resulting 368 bp subfragment containing both upstream activation sites is isolated. In an analogous manner, cleavage of the above BamHI-SalI fragment with BamHI and ClaI or with ClaI and BstEII yields the 268 bp BamHI-ClaI subfragment containing UAS1(PHO5) and the 100 bp ClaI-BstEII subfragment containing UAS2(PHO5), respectively. The isolation and purification of the fragments and subfragments is accomplished by conventional means, e.g. by agarose gel electrophoresis or polyacrylamide gel electrophoresis.

The DNA fragments containing the upstream activation sites according to the invention may be shortened in a manner known per se, e.g. by partial digestion with an exonuclease, for example Ba131, in such a manner that the UAS function in the shortened fragment is retained. Shortening may be effected at the 5' end or at the 3' end of the fragments or at either side. Selection of those subfragments having the UAS function retained is made as above, viz. by replacing the original sequences containing the UAS(s) by the shortened fragments and testing the resulting PHO5 promoter deletion mutants for their ability for effecting expression of the PHO5 structural gene. The fragments and the shortened derivatives thereof according to the invention containing one or both of the upstream activation sites of the PHO5 gene may be provided with synthetic linker sequences attached to either end to facilitate the construction of hybrid promoters and attachment to a vector.

The DNA fragments as well as the shortened derivatives thereof containing the upstream activation site(s) of PHO5 may also be produced by chemical DNA synthesis using conventional techniques which are well-known in the art. Appropriate techniques have been compiled by S. A. Narang [Tetrahedron 39, 3(1983)]. In particular, the methods described in European Patent Application No. 146,785 may be used and are herein incorporated by reference.

Further aspects of the present invention are the use of the upstream activation sites of the PHO5 gene for the production of hybrid promoters and hybrid promoters comprising upstream activation sites of the PHO5 gene.

The invention is especially directed to yeast hybrid promoters including, especially consisting of, a 5' upstream promoter element comprising upstream activation site(s) of the yeast PHO5 gene and a 3' downstream promoter element of a yeast gene other than the yeast PHO5 gene comprising transcription initiation sites including a functional TATA box and ending close to the translational start codon.

The 5' upstream promoter element is especially one of the DNA fragments specified above, in particular the 368 bp BamHI-BstEII fragments containing UAS1(-PHO5) and UAS2(PHO5), or the 268 bp BamHI-ClaI fragment containing UAS1(PHO5), or shortened derivatives thereof in which the UAS function is retained, such as the 31 bp fragment containing UAS1(PHO5) or even smaller subfragments thereof.

The 3' downstream promoter element is preferably derived from the promoter of a highly expressed yeast gene, especially from the promoter of a yeast gene coding for a glycolytic enzyme, such as the promoter of the enolase, glyceraldehyde-3-phosphate dehydrogenase (GAPDH), 3-phosphoglycerate kinase (PGK), hexokinase, pyruvate decarboxylase, phosphofructokinase, glucose-6-phosphate isomerase, 3-phosphoglycerate mutase, pyruvate kinase (PyK), triosephosphate isomerase, phosphoglucose isomerase and glucokinase genes. The 3' promoter elements include the TATA box which is involved in positioning the enzyme RNA polymerase II for correct transcription initiation and the correct start points of transcription (major mRNA startpoints). Downstream of the TATA box the 3' promoter element extends to the region between the major mRNA start and the translational start codon (ATG), preferably close to the translational start codon. At the upstream side of the TATA box the 3' promoter elements include approximately 50 to 150 original base pairs. The exact length of this upstream DNA sequence is not crucial since there appears to be some flexibility in the spacing between the UASs and the TATA box.

The preferred 3' promoter element of the present invention is derived from the GAPDH promoter which is known to be one of the strongest yeast promoters known in the art [the enzyme GAPDH can amount to about 5% of the dry weight of *S.cerevisiae*, cf. E. G. Krebs, J. Biol. Chem. 200, 471 (1953)]. Preferably, the 3' GAPDH promoter element starts at nucleotide −300 to −180 and ends at nucleotide −1 of the GAPDH gene. In one preferred embodiment of the invention, the 3' promoter element comprises nucleotides −199 to −1 of the GAPDH gene. In another preferred embodiment of the invention, the 3' promoter element comprises nucleotides −263 to −1 of the GAPDH gene.

The hybrid promoters of the present invention may contain a single UAS(PHO5) or multiple UAS(PHO5) of the same type, such as UAS1(PHO5), preferably arranged in head to tail orientation. With regard to the 3' promoter element the UAS(s) may have the same or the reversed orientation as compared to the orientation in the genuine PHO5 promoter.

The constituents of the hybrid promoters according to the present invention, viz. the promoter element containing UAS(s) of PHO5 and the promoter element containing the TATA box, are linked via synthetic linkers, by blunt end ligation or, if possible, via naturally occurring compatible restriction sites. The 5' and 3' termini of the hybrid promoters of the present invention are suitably provided with synthetic linkers which allow ligation to a vector DNA and, at the 3' end, attachment to a heterologous protein coding region.

The hybrid promoters according to the invention meet all requirements imposed on promoters usable in biotechnology. They are strong, inducible by substances different from essential carbon or nitrogen sources of the growth medium, and are conveniently handled on laboratory and industrial scale.

The present invention concerns also the method for producing hybrid promoters including a 5' upstream promoter element comprising upstream activation site(s) of the yeast PHO5 gene and a 3' downstream promoter element of a yeast gene other than the yeast PHO5 gene comprising transcription initiation sites including a functional TATA box and ending close to the translational start codon, which method comprises linking a 5' upstream promoter element containing upstream activation site(s) of the yeast PHO5 gene to a 3' downstream promoter element of a yeast gene other than the PHO5 gene including a functional TATA box and ending close to the translational start codon.

In a preferred embodiment of the present invention ligation of the promoter elements is effected through synthetic linkers.

The above downstream promoter elements of a yeast gene other than the PHO5 gene are produced by partially digesting the 5' end of a strong yeast promoter, for example one of those enumerated above, which extends to the region between the major mRNA start and the translational start codon, with an exonuclease, for example Bal31, and linking the resulting 5' blunt ends to a synthetic linker DNA. Promoter elements are selected which maintain transcription start site(s) and TATA box including about 50 to 150 base pairs of sequences 5' to the TATA box. Selection is performed, for example, by cleaving the resulting promoter elements with the restriction endonuclease recognizing the synthetic linker sequence at the 5' end and with the restriction endonuclease recognizing the synthetic linker sequence at the 3' end of the promoter element and determining the length of the resulting DNA fragment by means of agarose gel electrophoresis. The 3' promoter elements can also be produced by chemical synthesis using methods known in the art.

The hybrid promoters according to the invention can be used for the enhanced and regulated expression of mammalian genes in yeast.

2. Hybrid vectors containing a gene encoding a heterologous polypeptide under the control of hybrid promoters The invention relates also to yeast hybrid vectors containing one or multiple DNA inserts each comprising a DNA segment coding for a polypeptide heterologous to yeast under the transcriptional control of a hybrid promoter consisting of a 5' upstream promoter element with UAS(s) of the yeast PHO5 gene and a 3' downstream promoter element of a yeast gene other than the PHO5 gene comprising transcription initiation sites including a functional TATA box.

The hybrid vectors according to the invention are selected from the group consisting of a hybrid plasmid and a linear DNA vector.

A DNA segment coding for a polypeptide heterologous to yeast is a DNA (gene) coding for a wide variety of polypeptides, including glycosylated polypeptides, in particular of higher eukaryotic, especially mammalian, such as animal or especially human origin, such as enzymes which can be used, for example, for the production of nutrients and for performing enzymatic reactions in chemistry, or non-enzymatic polypeptides, which are useful and valuable for the treatment of human and animal diseases or for the prevention thereof, for example hormones, polypeptides with immunomodulatory, anti-viral and anti-tumor properties, antibodies, viral antigenes, vaccines, clotting factors, foodstuffs and the like.

Example of such polypeptides are insulin, growth factors, such as epidermal, insulin-like, mast cell, nerve or transforming growth factor, growth hormones, such as human or bovine growth hormones, interleukin, such as interleukin-1 or -2, human macrophage migration inhibitory factor (MIF), interferons, such as human $\alpha$-interferon, for example interferon-$\alpha$A, $\alpha$B, $\alpha$D or $\alpha$F, $\beta$-interferon, $\gamma$-interferon or a hybrid interferon, for example an $\alpha$A-$\alpha$D- or an $\alpha$B-$\alpha$D-hybrid interferon, hepatitis virus antigens, such as hepatitis B virus surface or core antigen or hepatitis A virus antigen, plasminogen activators, such as tissue plasminogen activator or urokinase, tumour necrosis factor, somatostatin, renin, $\beta$-endorphin, immunoglobulins, such as the light and/or heavy chains of immunoglobulin D, E or G, immunoglobulin binding factors, such as immunoglobulin E binding factor, calcitonin, human calcitonin-related peptide, blood clotting factors, such as factor IX or VIIIc, eglin, such as eglin C, desulphatohirudin, such as desulphatohirudin variant HV1, HV2 or PA, or human superoxide dismutase. Preferred genes are those coding for a human $\alpha$-interferon or hybrid interferon, human tissue plasminogen activator (t-PA), hepatitis B virus surface antigen (HBVsAg), insulin-like growth factor I, eglin C and desulphatohirudin variant HV1.

The hybrid promoter is especially one of those specified above.

The hybrid vectors according to the invention may contain one or multiple DNA inserts each comprising, inter alia, the hybrid promoter and a DNA segment coding for a polypeptide heterologous to yeast. If the hybrid vectors contain multiple DNA inserts, preferably 2 to 4 DNA inserts, these can be present in a tandem array or at different locations of the hybrid vector. Preferred hybrid vectors contain one DNA insert or DNA inserts in a tandem array.

In the hybrid vectors of the present invention, the yeast hybrid promoter is operably linked to the polypeptide coding region so as to ensure effective expression of the polypeptide. In one preferred embodiment of the present invention, the yeast hybrid promoter is directly linked to the coding region of the mature polypeptide with a translation start signal (ATG) inserted at the junction. A preferred region for joining the yeast hybrid promoter to the polypeptide coding region is the region immediately adjacent to the endogenous ATG.

In another preferred embodiment of the present invention, a signal sequence is included in the construction. Suitable signal sequences are, for example, the PHO5 signal sequence, that of the yeast invertase gene, or the $\alpha$-factor pre-pro sequence, and signal sequences naturally linked to the polypeptide coding region to be expressed. Alternatively, fused signal sequences may be constructed. Those combinations are favoured which allow a precise cleavage between the signal sequence and the mature polypeptide sequence. Additional sequences, such as pro- or spacer-sequences which may or may not carry specific processing signals can also be included in the constructions to facilitate accurate processing of precursor molecules. Alternatively fused proteins can be generated containing internal processing signals which allow proper maturation in vivo or in vitro. Preferably, the processing signals contain a Lys-Arg residue, which is recognized by a yeast endopeptidase located in the secretion pathway.

Upon expression of the gene, the gene product enters the secretory pathway and is transported to the periplasmic space. If further excretion through the cell wall into the culture medium can be achieved, a considerable increase in yields should be possible. Also the recovery process can be simplified with no cells to be disrupted. Furthermore, the polypeptide can be recovered without an additional methionine at the N-terminus, because there is no need for an ATG as a translation start signal in front of the mature coding sequence. Since glycosylation is associated with the secretory pathway the produced polypeptide is expected to be glycosylated (provided that glycosylation sites are present). There are several features which render glycosylated polypeptides advantageous over unglycosylated polypeptides: The glycosylated polypeptide resembles more closely the genuine polypeptide from mammalian cells than the unglycosylated polypeptide does. Furthermore, the tertiary structure of such proteins is probably depending to a certain degree on the presence of glycosyl residues. It is expected that carbohydrate residues present in these molecules have a favourable influence on chemical stability and on pharmacological activity.

Preferably, the hybrid vectors according to the invention comprise also the 3' flanking sequence of a yeast gene which contain the proper signals for transcription termination and polyadenylation. The preferred 3' flanking sequence is that of the yeast PHO5 gene.

The invention relates especially to a linear DNA molecule essentially consisting of a hybrid promoter consisting of a 5' upstream promoter element with UAS(s) of the yeast PHO5 gene and a 3' downstream promoter element of a yeast gene other than the PHO5 gene comprising transcription initiation sites including a functional TATA box, a DNA segment coding for a polypeptide heterologous to yeast which segment is controlled by said hybrid promoter, and a DNA segment containing properly located transcription termination signals of the yeast PHO5 gene.

By virtue of the homologous 3' and 5' flanking sequences the whole linear DNA vector including the polypeptide coding region is stably integrated at the PHO5 locus in the yeast chromosome.

The invention relates particularly to circular hybrid plasmids which apart from the hybrid promoter, the polypeptide coding region and 3' flanking sequences contain additional DNA sequence(s) which are inessential or less important for the function of the promoter, i.e. for the expression of the polypeptide coding region, but which may perform important functions, for example, in the propagation of the yeast cells transformed with said hybrid vectors. The additional DNA sequence(s) may be derived from prokaryotic and/or eukaryotic cells and may include chromosomal and/or extrachromosomal DNA sequences. For example, the additional DNA sequences may stem from (or consist of) plasmid DNA, such as bacterial or eukaryotic plasmid DNA, vital DNA and/or chromosomal DNA, such as bacterial, yeast or higher eukaryotic chromosomal DNA. Preferred hybrid plasmids contain additional DNA sequences derived from bacterial plasmids, especially *Escherichia coli* plasmid pBR322 or related plasmids, bacteriophage ε, yeast 2μ plasmid, and/or yeast chromosomal DNA.

In particular, the additional DNA sequences carry a yeast replication origin and a selective genetic marker for yeast. Hybrid plasmids containing a yeast replication origin,,e.g. a chromosomal autonomously replicating segment (ars), are extrachromosomally maintained within the yeast cell after transformation and are autonomously replicated upon mitosis. Hybrid plasmids containing sequences homologous to yeast 2μ plasmid DNA can be used as well. These hybrid plasmids will get integrated by recombination into 2μ plasmids already present within the cell or will replicate autonomously. 2μ sequences are especially suitable for high-frequency transformation plasmids and give rise to high copy numbers.

As to the selective gene marker for yeast, any marker gene can be used which facilitates the selection for transformants due to the phenotypic expression of the marker. Suitable markers for yeast are particularly those expressing antibiotic resistance or, in the case of auxotrophic yeast mutants, genes which complement host lesions. Corresponding genes confer, for example, resistance to the antibiotic cycloheximide or provide for prototrophy in an auxotrophic yeast mutant, for example the URA3, LEU2, HIS3 or TRP1 gene. It is also possible to employ as markers structural genes which are associated with an autonomously replicating segment providing that the host to be transformed is auxotrophic for the product expressed by the marker.

Advantageously, the additional DNA sequences which are present in the hybrid plasmids according to the invention also include a replication origin and a selective genetic marker for a bacterial host, especially *Escherichia coli*. There are useful features which are associated with the presence of an *E. coli* replication origin and an *E. coli* marker in a yeast hybrid vector: Firstly, large amounts of hybrid vector DNA can be obtained by growth and amplification in *E. coli* and, secondly, the construction of hybrid vectors is conveniently done in *E. coli* making use of the whole repertoire of cloning technology based on *E. coli*. *E. coli* plasmids, such as pBR322 and the like, contain both *E. coli* replication origin and *E. coli* genetic markers conferring resistance to antibiotics, for example tetracycline and ampicillin, and are advantageously employed as part of the yeast hybrid vectors.

The additional DNA sequence which contain, for example, replication origin and genetic markers for yeast and a bacterial host (see above) are hereinafter referred to as "vector DNA" which together with the yeast promoter and the polypeptide coding region is forming a hybrid plasmid according to the invention.

In a preferred embodiment, the present invention relates to hybrid plasmids capable of replication and phenotypical selection in a yeast host strain comprising a yeast hybrid promoter and a DNA sequence encoding a heterologous polypeptide, said DNA sequence being positioned together with transcription start and termination signals as well as translation start and stop signals in said hybrid plasmid under control of said hybrid promoter such that in a transformed yeast strain it is expressed to produce said polypeptide.

The hybrid vectors of the invention are prepared by methods known in the art, for example by linking a hybrid promoter consisting of a 5' upstream promoter element with UAS(s) of the yeast PHO5 gene and a 3' downstream promoter element of a yeast gene other than the PHO5 gene comprising transcription initiation sites including a functional TATA box, a DNA segment coding for a polypeptide heterologous to yeast and 3' flanking sequences of a yeast gene such that said DNA segment is under transcriptional control of said hybrid promoter, and optionally introducing one or more linear DNAs produced into a vector DNA.

Conveniently mapped linear or, preferably, circular vector DNA, for example bacterial plasmid DNA or the like (see above), having at least one restriction site, preferably two or more restriction sites, can be employed. Advantageously, the vector DNA already contains replication origins and gene markers for yeast and/or a bacterial host. The vector DNA is cleaved using an appropriate restriction endonuclease. The restricted DNA is ligated to the linear DNA fragment containing, inter alia, the yeast hybrid promoter and to the DNA segment coding for the polypeptide. Prior to or after linking of the hybrid promoter and the polypeptide coding region (or simultaneously as well), it is also possible to introduce replication origins and/or markers for yeast or a bacterial host. At all events, the restriction and annealing conditions are to be chosen in such a manner that there is no interference with the essential functions of the vector DNA and of the hybrid promoter. The hybrid vector may be built up sequentially or by ligating two DNA segments comprising all sequences of interest.

Various techniques may be used to join DNA segments in vitro. Blunt ends (fully base-paired DNA duplexes) produced by certain restriction endonucleases may be directly ligated with T4 DNA ligase. More usually, DNA segments are linked through their single-stranded cohesive ends and covalently closed by a DNA ligase, e.g. T4 DNA ligase. Such single-stranded "cohesive termini" may be formed by cleaving DNA with another class of endonucleases which produce staggered ends (the two strands of the DNA duplex are cleaved at different points at a distance of a few nucleotides). Single strands can also be formed by the addition of nucleotides to blunt ends or staggered ends using terminal transferase ("homopolymeric tailing") or by simply chewing back one strand of a blunt-ended DNA segment with a suitable exonuclease, such as ε-exonuclease. A further preferred approach to the production of staggered ends consists in ligating to the blunt-ended DNA segments a chemically synthesized linker DNA which contains a recognition site for a staggered-end forming endonuclease and digesting the resulting DNA with the respective endonuclease.

In order to be efficiently expressed, the gene must be properly located with respect to sequences containing transcriptional (yeast hybrid promoter) and translational functions. Firstly, the ligation of the DNA segment comprising the hybrid promoter with the polypeptide coding region has to be achieved in the proper orientation. If two orientations are possible the correct one is determined by conventional restriction analysis. Hybrid vectors containing an incorrectly oriented polypeptide gene insert are re-oriented by excising the gene insert with a suitable restriction endonuclease and re-ligating the gene with the hybrid vector fragment. In any case improper orientation is avoided by ligating two DNA segments each with different restriction sites at their ends. Furthermore, the construction of the hybrid vector should be done in such a way that it allows correct transcription initiation and termination. As to the latter point, the transcript should preferably end in a DNA sequence derived from yeast chromosomal DNA or yeast 2μ plasmid. Advantagously, the transcript ends in a DNA sequence containing transcription termination signals of a yeast gene, e.g. of PHO5 or TRP1. Secondly, a proper reading frame must be established. Ordinarily, the nucleotide sequence of the promoter region and the polypeptide coding region is known prior to ligation or can easily be determined so that there are no problems in establishing the correct reading frame.

If the direct expression of the mature polypeptide is desired, signal sequences or parts thereof optionally following the hybrid promoter region and/or optionally preceding the mature polypeptide coding region have to be eliminated, for example by digestion with an exonuclease, e.g. with Bal31. A preferred region for directly joining a yeast promoter to the polypeptide coding sequence is between the major mRNA start and the ATG translational start codon. For a junction in this region the polypeptide coding sequence should have its own ATG for translation initiation, or else it has to be provided with an additional synthetic oligonucleotide. The yeast hybrid promoter may also be linked to the polypeptide coding sequence by means of a synthetic oligodeoxynucleotide as a connecting molecule. Thus, the hybrid promoter region may be, if possible, restricted near its 3'-terminus so that it lacks a predetermined number of base pairs. Analogously, the polypeptide coding sequence may be restricted near its 5'-terminus. A synthetic oligodeoxynucleotide can then be constructed in such a way that, when joining the yeast hybrid promoter and the polypeptide coding sequence via the connecting oligodeoxynucleotide, the missing base pairs are restored including an ATG translation initiation signal and the polypeptide coding sequence is in the proper reading frame relative to the promoter.

The ligation mixture containing the desired hybrid vector is directly used in the transformation step or is first enriched for the hybrid vector, e.g. by gel electrophoresis, and then used for transformation.

Intermediate products, such as vectors still lacking one or more essential functions, as well as the final hybrid vectors according to the invention are optionally transformed into a bacterial host, especially E. coli, for the above reasons (e.g. production of large amounts of intermediate products and hybrid plasmids, respectively). Bacterial vectors, such as the E. coli plasmid pBR322 and those fragments thereof which contain a bacterial replication origin and gene marker(s) are the most preferred vectors for that reason. When using such a bacterial vector, the final steps for the preparation of the yeast hybrid vectors preferably also include the introduction of a genetic marker and a replication origin for yeast.

3. Transformation of yeast with hybrid vectors containing a polypeptide coding sequence Another aspect of the present invention involves a process for the production of transformed yeast cells capable of producing a polypeptide heterologous to yeast, which process comprises transforming yeast cells with a hybrid vector containing one or multiple DNA inserts each comprising a DNA segment coding for a polypeptide heterologous to yeast under the transcriptional control of a hybrid promoter consisting of a 5' upstream promoter element with UAS(s) of the yeast PHO5 gene and a 3' downstream promoter element of a yeast gene other than the PHO5 gene comprising transcription initiation sites including a functional TATA box.

Useful yeasts include species of the genera Saccharomyces, Kluyveromyces, Candida, Rhodotorula, Torulopsis and related genera [cf. J. Lodder, "The Yeasts", Amsterdam 1971], especially strains of Saccharomyces cerevisiae.

The transformation of yeast with the hybrid vectors may be accomplished by procedures known in the art, e.g. according to the method described by Hinnen et al [Proc. Natl. Acad. Sci. USA75, 1929(1978)]. This method can be divided into three steps:
(1) Removal of the yeast cell wall or parts thereof.
(2) Treatment of the "naked" yeast cells (spheroplasts) with the transforming DNA in the presence of PEG (polyethyleneglycol) and $Ca^{2+}$ ions.
(3) Regeneration of the cell wall and selection of the transformed cells in a solid layer of agar.

Preferred methods:

ad (1): The yeast cell wall is removed enzymatically using various preparations of glucosidases, such as snail gut juices (e.g. Glusulase ® or Helicase ®) or enzyme mixtures obtained from microorganisms (e.g. Zymolyase ®) in osmotically stabilized solutions (e.g. 1M sorbitol).

ad (2): The yeast spheroplasts aggregate in the presence of PEG and local fusions of the cytoplasmic membranes are induced. The generation of "fusion-like" conditions is crucial and many transformed yeast cells become diploid or even triploid during the process of transformation. Procedures which allow selection of fused spheroplasts can be used to enrich for transformants, i.e. transformed cells can easily be screened for among preselected fusion products.

ad (3): Since yeast cells without cell wall do not divide the cell wall has to be regenerated. This regeneration is conveniently done by embedding the spheroplasts into agar. For example, molten agar (about 50° C.) is mixed with the spheroplasts. Upon cooling the solution to yeast growth temperatures (about 30° C.), a solid layer is obtained. This agar layer is to prevent rapid diffusion and loss of essential macromolecules from the spheroplasts and thereby facilitates regeneration of the cell wall. However, cell wall regeneration may also be obtained (although at lower efficiency) by plating the spheroplasts onto the surface of preformed agar layers.

Preferably, the regeneration agar is prepared in a way to allow regeneration and selection of transformed cells at the same time. Since yeast genes coding for enzymes of amino acid biosynthetic pathways are generally used as selective markers (supra), the regeneration is preferably performed in yeast minimal medium agar. If very high efficiencies of regeneration are required following two step procedure is advantageous: (1) regeneration of the cell wall in a rich complex medium, and (2) selection of the transformed cells by replica plating the cell layer onto selective agar plates.

If the hybrid vector does not contain any marker gene the transformed cells can also be identified by means of alternative methods. Such methods include, for example, in situ hybridization with a labeled DNA fragment homologous to sequences of the hybrid vector [e.g. according to Hinnen et al., supra], in situ immunoassays provided that an antibody for the product of the introduced gene is available, or other screening methods which measure gene products encoded by the transforming plasmid(s).

Alternatively, the yeast can be co-transformed with a hybrid vector according to the invention and a second vector containing a genetic marker for yeast. If the two different vectors have DNA sequences in common (these can be bacterial sequences present on the vectors), recombination takes place leading to a fused selectable hybrid molecule.

The yeast can also be cotransformed with a linear DNA vector consisting of the yeast hybrid promoter, the heterologous polypeptide coding region controlled by said hybrid promoter and transcription termination signals of the yeast PHO5 gene, and a vector containing a selective marker for yeast. Cotransformation allows enrichment for those yeast cells which have taken up DNA that cannot be directly selected for. Since competent cells take up any type of DNA a high percentage of cells transformed with a selective vector will also harbor any additional DNA (such as the above linear DNA). By virtue of sufficient long homologous sequences (e.g. about 20 to 100 deoxynucleotides in length) the polypeptide gene will be stably integrated into the host chromosome. The specific construction of the present invention will lead to a stable integration of the heterologous gene at the chromosomal location of the PHO5 gene, viz. in yeast chromosome II.

The obtained yeast strains containing the hybrid plasmids according to the invention can be improved in production of heterologous polypeptides by mutation and selection using methods known in the art. The mutation can be effected, for example, by U.V. irradiation or suitable chemical reagents.

It is found that transformation with the hybrid vectors according to the invention and regeneration of the cell walls in rich media containing glucose as carbon source can be done conveniently and is substantially easier than the corresponding steps done with hybrid vectors containing conventional promoters inducible by glucose which have to be performed in glucose-free media in order to prevent accumulation of the potentially lethal gene product within the cells.

The invention also relates to yeast hosts transformed with hybrid vectors containing one or multiple DNA inserts each comprising a DNA segment coding for a polypeptide heterologous to yeast under the transcriptional control of a hybrid promoter consisting of a 5' upstream promoter element with UAS(s) of the yeast PHO5 gene and a 3' downstream promoter element of a yeast gene other than the PHO5 gene comprising transcription initiation sites including a functional TATA box, and to mutants thereof.

4. Cultivation of the transformed yeast cells and isolation of the expressed polypeptide The invention concerns furthermore a method for producing a polypeptide heterologous to yeast characterized in that a yeast strain transformed with a hybrid vector containing one or multiple DNA inserts each comprising a DNA segment coding for a polypeptide heterologous to yeast under the transcriptional control of a hybrid promoter consisting of a 5' upstream promoter element with UAS(s) of the yeast PHO5 gene and a 3' downstream promoter element of a yeast gene other than the PHO5 gene comprising transcription initiation sites including a functional TATA box, or a mutant thereof is cultured and the expressed polypeptide is isolated.

The transformed yeast cells according to the present invention are cultured by methods known in the art in a liquid medium containing assimilable sources of carbon, nitrogen, inorganic salts, and if necessary growth promoting substances.

Various carbon sources are usable. Examples of preferred carbon sources are assimilable carbohydrates, such as glucose, maltose, mannitol or lactose, or an acetate, such as sodium acetate, which can be used either alone or in suitable mixtures. Suitable nitrogen sources include, for example, amino acids, such as casamino acids, peptides and proteins and their degradation products, such as tryptone, peptone or meat extracts, furthermore yeast extract, malt extract, corn steep liquor, as well as ammonium salts, such as ammonium chloride, sulphate or nitrate, which can be used either alone or in suitable mixtures. Inorganic salts which may be used include for example sulphates, chlorides, phosphates and carbonates of sodium, potassium, magnesium and calcium. Additionally, the nutrient medium may also contain growth promoting substances. Substances which promote growth include, for example, growth promoters, trace elements, such as iron, zinc, manganese and the like, or individual amino acids.

Since the hybrid promoters according to the present invention are regulated, the composition of the nutrient medium has to be adapted to the growth phases. During the growth period, under high phosphate concentration the hybrid promoters according to the invention are substantially turned down. For example, the most preferred hybrid promoter of the invention which includes a 5' upstream promoter element of PHO5 with the UASs of PHO5 and a 3' downstream promoter element of GAPDH with the TATA box, is turned down about fifty-fold under these conditions. Therefore, potentially toxic gene products are only synthesised at very low rates and harmful effects on cell metabolism are minimized. When a sufficient cell density is reached the inorganic phosphate levels in the nutrient medium are preferably reduced (low $P_i$ medium). Thereupon the hybrid promoters according to the invention are turned on (derepressed) and maximum levels of mRNA transcripts are obtained.

The cultivation is carried out by employing conventional techniques. The culturing conditions, such as temperature, pH of the medium and fermentation time are selected in such a way that maximal levels of the desired polypeptide are produced. In general growth is performed under aerobic conditions in submerged culture with shaking or stirring at a temperature of about 25° to 35° C., at a pH value of from 4 to 8, for example at approximately pH 7, and for about 4 to 20 hours, preferably until maximum yields of the desired proteins are reached.

The isolation and purification of the expressed polypeptide, if desired, is performed according to methods known in the art.

After the transformed cells have been grown to a satisfactory cell density, the first step for the recovery of the expressed protein consists in liberating the protein from the cell interior. In most procedures the cell wall is first removed by enzymatic digestion, e.g. with glucosidases. Subsequently, the resulting spheroplasts are treated with detergents, such as Triton. Alternatively, mechanical forces, such as shearing forces (for example X-press, French-press) or shaking with glass beads, are suitable for breaking cells. The resulting mixture is enriched for the desired polypeptide by conventional means, such as removal of most of the non-proteinaceous material by treatment with polyethyleneimine, precipitation of the proteins by saturating the solution with ammonium sulphate or trichloroacetic acid, gel electrophoresis, dialysis, chromatography, for example, ion exchange chromatography, size-exclusion chromatography, HPLC or reverse phase HPLC, molecular sizing on a suitable Sephadex ® column, or the like. The final purification of the pre-purified product is achieved, for example, by means of antibody affinity chromatography.

In the case where the desired polypeptide is secreted by the yeast cell into the periplasmatic space, a simplified protocol can be used: The polypeptide may be recovered without cell lysis by enzymatic removal of the cell wall or by treatment with chemical agents, e.g. thiol reagents or EDTA, which give rise to cell wall damages permitting the polypeptide to be released. In the case where the polypeptide is secreted into the culture broth, it can be recovered directly therefrom.

A mixture of glycosylated and unglycosylated proteins obtained may be separated, for example, by chromatography on a concanavalin-A Sepharose ® column. Unglycosylated products will pass through the column whereas glycosylated products will selectively adsorb and can be eluted by conventional means, e.g. α-methylmannoside in combination with a chaotropic agent, such as KSCN.

It is also possible to remove glycosyl residues enzymatically, e.g. by the action of endoglycosidase H or F. This method permits the production of unglycosylated products in substantially pure form.

The invention concerns furthermore the polypeptides whenever prepared according to the methods of the present invention.

The invention concerns especially the upstream activation sequences of PHO5, the hybrid promoters, the hybrid vectors, the transformed yeast cells and the processes for the preparation thereof as well as the method for producing polypeptides heterologous to yeast as described in the Examples.

BRIEF DESCRIPTION OF THE DRAWINGS

In the following experimental part various embodiments of the present invention are described with reference to the accompanying drawings in which:

FIG. 1 shows the DNA sequence of the BamHI-SalI fragment of the PHO5 promoter region.

FIG. 2 provides the DNA sequence of the promoter region of GAPDH [clone 491, cf. G. A. Bitter et al., Gene 32, 263(1984)].

FIG. 3 depicts schematically the production of plasmid pGAPDH-EL.

FIG. 4 depicts 3′ promoter elements of the GAPDH gene used in the present invention.

FIG. 5 is a diagram showing the production of plasmid pJDB207R/PHO5-EGL.

FIG. 6 shows the construction of plasmid pJDB207/PAPEL-EGL(UAS1).

FIG. 7 is a schematic diagram showing the isolation of a DNA fragment coding for mature desulphatohirudin.

FIG. 8 shows schematically the manufacture of plasmid pJDB207/PHO5-HIR.

FIG. 9 shows schematically the construction of plasmid pJDB207/PHO5(Eco)-HIR.

FIG. 10 is a schematic diagram showing the construction of plasmid pJDB207/PAPFL-TPA(UAS1+UAS2).

The following Examples serve to illustrate the present invention but should not be construed as a limitation thereof.

EXPERIMENTAL PART

EXAMPLE 1

Construction of PHO5 Promoter Deletions a) Ba131 digestion

Recombinant phage M13mp9/PHO5 Bam-Sal containing the BamHI-SalI fragment of PHO5 depicted in FIG. 1 is used as a source for the PHO5. promoter (see European Patent Application No. 143,081). 20 μg of the phage DNA (RF: replicative form) are digested with restriction endonuclease SalI, resulting in a linear DNA of approximately 9 kb. After extraction with phenol/chloroform, the DNA is precipitated with ethanol. The DNA is resuspended in 10 mM Tris pH 8.0 at a concentration of 0.5 μg/ml. 16 μg of SalI cleaved DNA are digested with 2 U of exonuclease Ba131 (BRL) in 100 μl of 20 mM Tris pH 8.0, 199 mM NaCl, 12 mM MgCl$_2$, 12 mM CaCl$_2$ and 1 mM EDTA. Aliquots of 2 μg DNA each are withdrawn after 1, 2, 3, 4, 5 and 6 min. of incubation at 30° C. and are immediately mixed with 50 μl phenol and 60 μl TNE. After extraction with phenol/chloroform and ethanol precipitation, the DNA is resuspended in 10 mM Tris pH 8.0 at a concentration of 100 μg/ml. To analyse the extent of exonucleolytic cleavage by Ba131 0.5 μg of DNA from each time point are digested with endonuclease BamHI and analysed on a 1.5% agarose gel in Tris-borate buffer pH 8.3 (90 mM Tris.HCl pH 8.3, 90 mM boric acid, 2.5 mM EDTA). On the average 100 bp are removed from each end of the fragment per 1 min. of Ba131 digestion.

b) Addition of EcoRI linkers to the Ba131 treated DNA

Two A$_{260}$ units of EcoRI linkers (5′-GGAATTCC-3′, BRL) are resuspended in 250 μl of 10 mM Tris pH 8, 1 mM EDTA. Two μg of EcoRI linkers are kinased in 75 μl of 60 mM Tris pH 7.5, 10 mM MgCl$_2$, 15 mM DDT, 10 pM ATP and 33 U of T4 polynucleotide kinase (Boehringer). After 1 h at 37° C. the mixture is allowed to cool to room temperature and is then stored at −20° C.

The annealed, double stranded EcoRI linkers are ligated with their blunt ends to the Ba131 treated DNA fragments. Half a microgram of Ba131 treated DNA (see Example 1a) is incubated for 16 hours at room temperature with a 50 fold excess of kinased EcoRI linkers in 20 μl of 60 mM Tris pH 7.5, 10 mM MgCl$_2$, 10 mM DTT, 4 mMATP and 600 U of T4 DNA ligase (Biolabs). After inactivation of the T4 DNA ligase (10 min at 65° C.) the excess of EcoRI linkers is cleaved by 50 U of EcoRI (Boehringer) in a volume of 50 μl. The DNA is extracted with phenol/chloroform, precipitated by ethanol and resuspended in 10 mM Tris, 1 mM EDTA (m TE). Then, the DNA is cleaved with 5 units of BamHI (Biolabs) and the mixture is applied to a 1.5% low melting agarose gel (Sigma) in Tris-borate buffer (see above). The bands are stained with ethidium bromide and visualized under long wave UV light at 366 nm. The broad diffuse banding patterns between about 100 bp to 600 bp is cut out of the gel and the DNA is extracted as follows: The piece of agarose is liquified at 65° C., adjusted to 500 mM NaCl and incubated at 65° C. for 20 min. One volume of phenol (equilibrated with 10 mM Tris.HCl pH 7.5, 1 mM EDTA, 500 mM NaCl) is added. The aqueous phase is reextracted twice with phenol and once with chloroform. The DNA is precipitated with 2.5 volumes of cold absolute ethanol and collected by centrifugation. The DNA pellet is washed with cold 80% ethanol and then dried in vacuum. The DNA is resuspended in 10 μl TE.

c) Ligation into M13mp9

3 μg of RF of M13mp9 is digested with 15 units EcoRI (Biolabs) and 15 units BamHI (Boehringer) in a volume of 50 μl. After phenol extraction and ethanol precipitation the DNA is resuspended in 50 μl TE. Five μl of cut vector DNA (about 200 ng) are mixed with 10 μl of the above samples (DNA fragments resulting from various Ba131 digests as described in Example 1b) and ligated in a total volume of 20 μl in the presence of 60 mM Tris/HCl pH 7.5, 6 mM MgCl₂, 10 mM DTT, 1 mM ATP and 200 U of T4 DNA ligase for 15 hours. Transduction of competent cells of the strain *E. coli* JM101 is done according to the manual "M13 cloning and sequencing system" published by New England Biolabs. Phages from a number of white plaques are grown and analyzed for the size of their DNA inserts by cleavage with restriction enzymes EcoRI and BamHI.

d) Determination of Ba131 deletion end points by Sanger sequencing (deletions from the SalI site)

Sequencing is done using the dideoxy DNA sequencing system of Sanger et al. [Proc. Natl. Acad. Sci. USA 74, 5463(1977)] as described in the above mentioned manual. The deletion end points are given below:

| clone | position of last nucleotide of the PH05 sequence (see FIG. 1) |
|---|---|
| A | −502 |
| B | −471 |
| C | −422 |
| D | −400 |
| E | −392 |
| F | −369 |
| G | −350 |
| H | −328 |
| I | −300 |
| K | −283 |
| L | −255 |
| M | −226 |
| N | −211 |
| O | −187 |
| P | −111 |
| Q | −88 |
| R | −57 |
| S | −33 | e) Determination of Ba131 deletion end points by Sanger sequencing (deletions from the BamHI site)

A similar set of Ba131 deletions is done as described under a–c, except that M13mp9 PHO5 Bam-Sal is cut by BamHI. The Ba131 digested molecules are cut by EcoRI and SalI, and the generated fragments are cloned into M13mp9 digested with EcoRI and SalI. The deletion end points are given below:

| clone | position of last nucleotide of the PH05 sequence (see FIG. 1) |
|---|---|
| A' | −24 |
| B' | −35 |
| C' | −41 |
| D' | −48 |
| E' | −74 |
| F' | −89 |
| G' | −93 |
| H' | −97 |
| I' | −124 |
| K' | −162 |
| L' | −174 |
| M' | −262 |
| N' | −277 |
| O' | −306 |
| P' | −332 |
| Q' | −346 |
| R' | −361 |
| S' | −382 |
| T' | −393 | f) Construction of internal PHO5 promoter deletions

The Ba131 deletion set described under d) produces a "left arm" PHO5 promoter fragment ending with an EcoRI site and the Ba131 deletion set described under e) produces a "right arm" PHO5 promoter fragment ending with an EcoRI site. By combining "left arms" and "right arms" of various positions internal deletions are created which contain an EcoRI linker segment at the site of the deleted DNA. The individual internal deletions are constructed by cutting the "left arms" and "right arms" from the M13mp9 derivatives by restriction endonucleases EcoRI and BamHI (left arms) or EcoRI and SalI (right arms) and isolating the corresponding fragments via soft agarose gel electrophoresis as described under b). Equimolar amounts of "left arms", "right arms" and 200 ng BamHI and SalI digested M13mp9 vector DNA are ligated as described under c). After transduction into *E. coli* JM101 white plaques are picked, RF is produced and analyzed by restriction analysis (BamHI, SalI, EcoRI). The following arms are combined to create specific internal deletions (for numbering of the nucleotides cf. FIG. 1):

| "left arm" | "right arm" | deletion | from–to | number of nucleotides deleted |
|---|---|---|---|---|
| A | T' | Δ7 | −501 to −394 | 108 |
| B | T' | Δ8 | −470 to −394 | 77 |
| C | T' | Δ9 | −421 to −394 | 28 |
| D | S' | Δ10 | −399 to −383 | 17 |
| E | R' | Δ11 | −391 to −362 | 30 |
| F | Q' | Δ12 | −368 to −347 | 22 |
| G | P' | Δ13 | −349 to −333 | 17 |
| H | O' | Δ14 | −327 to −307 | 21 |
| I | N' | Δ15 | −299 to −278 | 22 |
| K | M' | Δ16 | −282 to −263 | 20 |
| L | L' | Δ17 | −254 to −175 | 80 |
| M | L' | Δ18 | −225 to −175 | 51 |
| N | L' | Δ19 | −210 to −175 | 36 |
| O | L' | Δ20 | −186 to −175 | 12 |
| O | K' | Δ21 | −186 to −163 | 24 |
| O | I' | Δ22 | −186 to −125 | 62 |
| O | H' | Δ23 | −186 to −98 | 89 |
| P | H' | Δ24 | −110 to −98 | 13 |
| P | G' | Δ25 | −110 to −94 | 17 |
| P | F' | Δ26 | −110 to −90 | 21 |
| Q | E' | Δ27 | −87 to −75 | 13 |
| R | D' | Δ28 | −56 to −49 | 8 |
| R | C' | Δ29 | −56 to −42 | 15 |
| R | B' | Δ30 | −56 to −36 | 21 |

| "left arm" | "right arm" | deletion | from-to | number of nucleotides deleted |
|---|---|---|---|---|
| — S | A' | Δ31 | −32 to −25 | 8 |

EXAMPLE 2

In Vivo Analysis of the Internal Deletions of The PHO5 Promoter

The various deletions described in Example 1f) are cloned into plasmid pJDB207/PHO5 [R. Haguenauer-Tsapis and A. Hinnen, Molecular and Cellular Biology, 4, 2668–2675(1984)] by replacing the wild type PHO5 Bam-Sal fragment with the deleted version. After transformation of yeast strain S.cerevisiae AH216 (cf. European Patent Application No. 143,081) the acid phosphatase activity is determined as described by Toh-e et al. [J. Bacteriol. 113, 727(1973)]. Deletions Δ11 and Δ12 show about a 10-fold reduction of PHO5 activity and define an upstream region ("upstream activation site", UAS) which is essential for PHO5 expression. A similar down effect is observed for deletion Δ17 (about 5-fold reduction) and for the TATA box deletions Δ23–Δ26 (about 30-fold reduction). All other deletions show activities of approximately wild type level. These results suggest that three areas of essential information for PHO5 expression are located at the following positions:

1. between positions −349 and −383 (UAS1)
2. between positions −225 and −263 (UAS2)
3. between positions −87 and −125 (TATA box)

DNA fragments containing the UAS1 or UAS2 or UAS1 and UAS2 of PHO5 can be produced from recombinant phage M13mp9/PHO5 Bam-Sal (cf. Example 1) by cleavage with appropriate restriction endonucleases. UAS1 is contained in a 268 bp BamHI-ClaI fragment having the formula

```
GATCCGAAAGTTGTATTCAACAAGAATGCGCAAATATGTCAACGTATTTGGAAGTCATCTTATGTG
CGCTGCTTTAATGTTTTCTCATGTAAGCGGACGTCGTCTATAAACTTCAAACGAAGGTAAAAGGTT
CATAGCGCTTTTTCTTTGTCTGCACAAAGAAATATATATTAAATTAGCACGTTTTCGCATAGAACG
CAACTGCACAATGCCAAAAAAAGTAAAAGTGATTAAAAGAGTTAATTGAATAGGCAATCTCTAAAT
GAAT,
```

UAS2 is contained in a 100 bp ClaI-BstEII fragment having the formula

```
CGATACAACCTTGGCACTCACACGTGGGACTAGCACAGACTAAATTTATGATTCTGGTCCCTGTTTT
CGAAGAGATCGCACATGCCAAATTATCAAATTG
``` and both UAS1 and UAS2 are present in the 368 bp BamHI-BstEII fragment having the formula −180 [UAS2(PHO5)] of the PHO5 gene possible candidates for UAS with regulating functions. UAS1(PHO5) is contained in a 268 bp BamHI-ClaI fragment whereas both UAS1(PHO5) and UAS2(PHO5) are contained in a 368 bp BamHI-BstEII fragment. These two fragments are each fused to two different GAPDH downstream promoter elements which include the TATA box and transcription initiation sites of GAPDH.

a) Construction of a yeast gene library

Thirty μg of total high molecular weight yeast DNA [M. V. Olsen et al. J. Mol. Biol. 132, 387 (1979)] from wild type Saccharomyces cerevisiae strain S288C is incubated for 30 min at 37° C. with 2 units of EcoRI methylase (New England Biolabs) in 250 μl of EcoRI methylation buffer as recommended by the supplier. DNA is precipitated by ethanol, resuspended in 500 μl of 25 mM Tris.HCl pH 8.5, 2 mM $MgCl_2$ (EcoRI* buffer) [H. Meyer, FEBS Lett. 90, 341 (1979)] and digested with EcoRI (Boehringer) until the size distribution of the DNA fragments has a maximum in the 30–50 kb range (a XhoI digest of XDNA provides appropriate 33 kb and 17 kb markers). The yeast DNA digested under EcoRI* conditions is size-fractionated on a sucrose gradient (5–20% sucrose in 10 mM Tris.HCl pH 7.5, 1 mM EDTA) for 6 hrs at 38'000 rpm in a SW 40 rotor. Thirty fractions of 0.4 ml each are collected from the top of the gradient. Fraction 16 contains DNA fragments of 30–40 kb in size. The DNA of this fraction (3 μg) is precipitated with ethanol and ligated for 16 hours at 15° C. in a total volume of 15 μl to 1 μg of cosmid vector pYcl [B. Hohn et al. in "Genetic Engineering", Vol. 2, p. 169, New York 1980] linearized by EcoRI. Ligation is carried out with 300 U T4 DNA ligase (New England Biolabs) using the buffer system described by the supplier. The DNA is packaged in vitro into bacteriophage ε [B. Hohn in "Methods in Enzymology", Vol. 68, p. 299, New York 1979] and the assembled phages are used to transduce E. coli strain HB101 ($r_k\ominus$, $m_k\ominus$, leu$\ominus$, pro$\ominus$, recA). The efficiency of transduction is about 5000 ampicillin-resistant colonies per μg of pYcl vector.

3000 amp colonies are picked and grown individually

```
GATCCGAAAGTTGTATTCAACAAGAATGCGCAAATATGTCAACGTATTTGGAAGTCATCTTATGTGC
GCTGCTTTAATGTTTTCTCATGTAAGCGGACGTCGTCTATAAACTTCAAACGAAGGTAAAAGGTTCA
TAGCGCTTTTTCTTTGTCTGCACAAAGAAATATATATTAAATTAGCACGTTTTCGCATAGAACGCAA
CTGCACAATGCCAAAAAAAGTAAAAGTGATTAAAAGAGTTAATTGAATAGGCAATCTCTAAATGAAT
CGATACAACCTTGGCACTCACACGTGGGACTAGCACAGACTAAATTTATGATTCTGGTCCCTGTTTT
CGAAGAGATCGCACATGCCAAATTATCAAATTG.
```

EXAMPLE 3

Construction of Fused PHO5—GAPDH Hybrid Promoters

Example 1 and 2 make a region around position −365 [UAS1(PHO5)] and another region around position in the wells of microtiter dishes in LB medium [10 g Bacto-Tryptone (Difco), 5 g Bacto Yeast Extract (Difco), 10 g NaCl] containing 100 μg/ml ampicillin.

b) Isolation of the yeast GAPDH gene

The gene library described above is screened with a synthetic oligonucleotide [prepared using the phosphotriester method: K. Itakura et. al., J. Am. Chem. Soc. 97, 7327 (1975); J. F. M. de Rooij et al., Recl. Trav. Chim. Pays-Bas 98, 537 (1979)] of the following structure: 5′-GCTCCATCTTCCACCGCCCC-3′. 10 μg of the oligonuclotide are kinased using 10 μl of γ-$^{32}$P-ATP (3000 Ci/mmol, 10 μCi/μl Amersham) with T4 polynucleotide kinase (Boehringer) in a total volume of 50 μl as described by Maniatis et al. ["Molecular Cloning", Cold Spring Harbor Lab., 1982, page 125]. Colony hybridization is performed as described by the same author (page 312). Positive clones are detected by autoradiography using Kodak X-5 X-ray film. Plasmid DNA isolation (see European Patent Application Nr. 100,561) produces a hybrid clone which contains a 2100 bp HindIII fragment coding for GAPDH [J. P. Holland et al., J. Biol. Chem. 254, 9839 (1979)]. Final proof for the authenticity of the cloned DNA comes from DNA sequencing experiment using the above mentioned oligonucleotide in combination with the dideoxy sequencing protocol as described by G. F. Hong [Bioscience Reports 1, 243 (1981)] for double stranded DNA. The cloned GAPDH gene has the same sequence as pgap491 published by Holland et al. [J. Biol. Chem. 255, 2596 (1980)].

c) preparation of the GAPDH downstream promoter elements (see FIGS. 2 and 3)

The 649 bp TaqI fragment which includes position −27 to −675 from the ATG of the GAPDH gene (see FIG. 2) is isolated by digesting the above mentioned hybrid plasmid with TaqI (New England Biolabs), separating the DNA fragments on a 1.2% soft agarose gel and extracting the DNA by hot phenol (see example 1). Cloning of the TaqI fragment is done into the ClaI site of pBR322: 1 μg of pBR322 is cleaved with three units of ClaI (New England Biolabs) as described by the supplier. 300 ng of the phenolized and cut vector is ligated to about 300 ng of insert DNA (649 bp Taq fragment) using 200 U of T4 DNA ligase in a total volume of 20 μl (see example 1b). Transformation is done into E. coli HB101 for ampicillin resistance, plasmid DNA is prepared and analyzed by restriction analysis [TaqI, DraI]. The orientation of the TaqI fragment is established using restriction endonuclease DraI'in combination with the BamHI site of the plasmids and a plasmid is selected which has the TaqI site of position −675 close to the HindIII site of pBR322. This plasmid designated pBR322/GAPDH is linearized using BamHI (New England Biolabs), and a digestion with Bal31 is performed as described in example 1 except that BglII linkers (5′-CAGATCTG-3′, New England Biolabs) are used and the digested plasmid is directly circularized at a concentration of 5 μg/ml in a total volume of 20 μl. The size of the Bal31 shortened TaqI fragment is determined by restriction analysis (using BglII and HindIII). Two clones are selected which contain DNA fragments which extend about 200 bp and 265 bp from the ATG upstream into the GAPDH promoter. Both fragments contain the presumptive TATA box at about −140 bp. These clones still contain the origin of replication in the pBR322 derived part of the DNA and are named pGAPDH-F and pGAPDH-E, respectively.

d) Combining the downstream GAPDH element with UAS1(PHO5) of PHO5 and the protein coding region of eglin C.

I) GAPDH elements (see FIG. 3)

In order to extend the GAPDH promoter elements from the TaqI site at position −27 to a position immediately adjacent to the ATG of the GAPDH gene two synthetic complementary oligonucleotides of the following structure are synthesized:

| 5′ | CGAATAAACACACATAAATAAAG | 3′ |
|---|---|---|
| 3′ | TTATTTGTGTGTATTTATTTCTTAA | 5′ |

These oligonucleotides provide the genuine GAPDH promoter sequence from position −26 to position −5 with the generation of a terminal EcoRI site. Two μg each of plasmids pGAPDH-E and -F are digested with 6 units of TaqI in 50 μl and the resulting mixtures are phenolized, ethanol precipitated and resuspended in 10 μl of water. The synthetic oligonucleotides are annealed by mixing 2 μl of each single strand in 100 μl of a solution containing 10 mM Tris.HCl pH 7.5, 10 mM MgCl₂, 50 mM NaCl, heating for 3 min. to 90° C. and slowly cooling the solution to room temperature (within about 3 hours). One μg each of the TaqI digested plasmids is mixed with about a twenty fold molar excess of the annealed oligonucleotides in a volume of 20 μl for about 18 hours using 800 U of T4 DNA ligase. The whole mixture is digested with 3 units of BglII (New England Biolabs). The DNA fragments are separated on a 1.5% soft agarose gel. The BglII-EcoRI fragments of about 200 bp and 265 bp, respectively, are cut from the gel, extracted and ethanol precipitated.

Plasmid pGAPDH-E is digested with BglII and EcoRI and the large (about 3.5 kb) fragment is isolated. This fragment is used as vector to clone the 265 bp and the 200 bp BglII-EcoRI fragments using ligation, transformation and plasmid isolation conditions as described above. The plasmids produced are designated pGAPDH-EL and pGAPDH-FL. The DNA sequences of the BglII-EcoRI fragments cloned in pGAPDH-EL and pGAPDH-FL are shown in FIG. 4. The exact size of the fragments is 266 bp and 201 bp, respectively.

II) The UAS1(PHO5) regulatory element

3 μg of plasmid p31/Y (see European Patent Application No. 100,561) are digested with 6 units of ClaI (New England Biolabs). The 3′ recessed ends are filled in a reaction with the Klenow fragment of E. coli DNA polymerase I (Bethesda Research Laboratories) according to Maniatis (supra). BglII linkers (5′-CAGATCTG-3′) are added as described in example 1. The DNA is digested with SalI and BglII (New England Biolabs) and run on a 1% soft agarose gel. The 548 bp fragment is cut from the gel, phenolized and ethanol precipitated as described above.

III) Construction of plasmid pJDB207R/PHO5-EGL (see FIG. 5)

This plasmid is a source of a DNA fragment composed of the eglin C coding region and the PHO5 transcription terminator.

A) Isolation of the DJDB207 vector fragment:

Six μg of plasmid pJDB207R/IF(α-3) (European Patent Application No. 100,561) are digested to completion with restriction endonuclease BamHI. The resulting DNA fragments of 6.85 kb and 1.15 kb in size are precipitated by ethanol and resuspended in 400 μl of 50 mM Tris-HCl pH 8.0. 4,5 units of calf intestine alkaline phosphatase (Boehringer, Mannheim) are added. The mixture is incubated for 1 hour at 37° C. Subsequently, the phosphatase is inactivated by incubation at 65° C. for 1 hour. The solution is adjusted to 150 mM NaCl.

The DNA solution is applied to a 100 μl bed of DE 52 (Whatman) anion exchanger equilibrated with 10 mM Tris-HCl pH 7.5 containing 150 mM NaCl and 1 mM EDTA. After washing with the same buffer, the DNA is eluted with 400 μl of 1.5M NaCl, 10 mM Tris-HCl pH 7.5, 1 mM EDTA and precipitated by ethanol. The large 6.85 kb BamHI fragment is separated from the small fragment on a 0.6% low melting agarose gel in Tris-borate-EDTA buffer pH 8.3.

B) Isolation of a 534 bp PHO5 promoter fragment

Ten μg of plasmid p31/R (European Patent Application No. 100,561) are digested with restriction endonucleases EcoRI and BamHI. The resulting 3 fragments are separated on a 0.6% low melting agarose gel in Tris-borate-EDTA buffer pH 8.3. A 534 bp BamHI-EcoRI fragment is isolated which contains the PHO5 promoter including the mRNA start sites.

C) Isolation of a 221 bp DNA fragment containing the coding sequence for eglin:

Eight μg of plasmid pML147 (European Patent Application No. 146,785) are digested with restriction endonucleases BamHI and EcoRI. The resulting two DNA fragments are separated on a 0.6% low melting agarose gel in Tris-borate-EDTA buffer pH 8.3. The 221 bp fragment is isolated.

D) Ligation of DNA fragments:

Three DNA fragments described above (Examples 3dIIIA-C) with appropriate sticky ends are ligated in one reaction: 0.1 pmole (0.45 μg) of the 6.85 kb BamHI vector fragment, 0.2 pmole (70 ng) of the 534 bp BamHI-EcoRI PHO5 promoter fragment and 0.2 pmole (29 ng) of the 221 bp EcoRI-BamHI fragment of pML147 are ligated. All three DNA fragments are contained in small gel blocks of low melting agarose. The three pieces of agarose gel are pooled, liquified at 65° C. and diluted 2 times. The ligation is done in a total volume of 270 μl of 60 mM Tris-HCl pH 7.5, 10 mM MgCl$_2$, 10 mM DTT, 1 mMATP with 16 units of T4 DNA ligase (Boehringer, Mannheim) at 15° C. for 16 hours. A 10 μl aliquot of the ligation mixture is added to 100 μl of calcium treated, transformation competent *E. coli* HB101 cells.

24 transformed, amp$^R$ colonies are grown individually in LB medium containing 100 μg/ml of ampicillin. Plasmid DNA is prepared according to the method of Holmes et al. [Anal. Biochem. 114, 193 (1981)] and is analysed by HindIII/EcoRI double digestion. The appearance of a 600 bp EcoRI-HindIII fragment indicates that the particular clone has the PHO5 promoter—eglin C—DNA fragment inserted in the expression vector in the correct orientation. As expected, about 50% of the clones have an insert in the right orientation. One of these clones is isolated and referred to as pJDB207R/PHO5-EGL.

Six μg of plasmid pJDB207R/PHO5-EGL are digested to completion with restriction endonucleases HindIII and SalI. The large 6.1 kb (vector part) fragment is isolated by soft agarose gel electrophoresis, phenol extraction and ethanol precipitation. The vector DNA is resuspended in 20 μl of water. The eglin fragment is created by digesting pJDB207R/PHO5-EGL with HindIII and EcoRI. The resulting 600 bp fragment is separated by soft agarose gel electrophoresis, phenol extracted and ethanol precipitated. The eglin fragment is resuspended in 20 μl H$_2$O.

IV) Ligation of the fragments using UAS1(PHO5) elements (see FIG. 6)

Ligation is performed using the following four components: 0.5 μg of the 6.1 kb HindIII-SalI vector fragment, 100 ng of the 600 bp EcoRI-HindIII eglin C fragment, 200 ng of the 266 bp BglII-EcoRI fragment of pGAPDH-EL and 100 ng of the 548 bp SalI-BglII fragment comprising UAS1(PHO5). Ligation is performed as above. Transformation of *E. coli* HB101 for ampicillin resistance, plasmid isolation and restriction analysis of positive clones is performed as described previously, using restriction endonucleases HindIII, EcoRI, BglII and SalI. One positive clone is selected and designated pJDB207/PAPEL-EGL (UAS1).

An analogous construction is done with the 201 bp BglII-EcoRI fragment of pGAPDH-FL. The plasmid produced is called pJDB207/PAPFL-EGL (UAS1).

V) Construction of hybrids with UAS1(PHO5) and UAS2(PHO5) elements

3 μg of the above plasmids (see IV) are digested with BglII. After phenol extraction and ethanol precipitation the DNA is resuspended in water. The 3' recessed ends are filled in with Klenow DNA polymerase as described under II). The plasmids are heated at 70° C. for 10 min. to inactivate the enzyme. After digestion with SalI (Biolabs) the large fragments (about 7.2 kb) are isolated by soft agarose gel electrophoresis and phenol extraction and the ethanol precipitated DNA is resuspended in water.

In a similar manner plasmid p31/Y is digested with BstEII, treated with DNA polymerase (Klenow fragment) and cleaved with SalI. The 651 bp fragment is isolated as described above. Ligation of 200 ng of the above vector DNAs with the 651 bp fragment yields the following plasmids:

pJDB207/PAPEL-EGL (UAS1+UAS2) (comprising the 266 bp BglII-EcoRI fragment from pGAPDH-EL)

pJDB207/PAPFL-EGL (UAS1+UAS2) (comprising the 201 bp BglII-EcoRI fragment from pGAPDH-FL).

EXAMPLE 4 a) Transformation of *Saccharomyces cerevisiae* GRF18

The four plasmids of example 3dIV and 3dV are each introduced into *Saccharomyces cerevisiae* strain GRF18 (α, his3-11, his3-15, leu2-3, leu2-112, can$^R$) using the transformation protocol described by Hinnen et al. [Proc. Natl. Acad. Sci. USA 75, 1929 (1978)]. Transformed yeast cells are selected on yeast minimal media plates deficient in leucine. Single transformed yeast colonies are isolated and referred to as *Saccharomyces cerevisiae* GRF18/pJDB207/PAPEL-EGL (UAS1), /PAPFL-EGL (UAS1), /PAPEL-EGL (UAS1+UAS2) and /PAPFL-EGL (UAS1+UAS2).

b) Fermentation of the transformants

Cells of the four *S.cerevisiae* GRF18 transformants are each grown in 10 ml of yeast minimal medium (Difco Yeast Nitrogen Base without aminoacids to which 2% glucose and 20 mg/l L-histidine are added) in a 50 ml Erlenmeyer flask with shaking at 30° C. for 24-hours to a density of $3 \times 10^7$ cells/ml. The cells are washed in 0.9% NaCl and used to inoculate 50 ml of a high P$_i$ medium (as above) and of a low P$_i$ minimal medium prepared according to the recipe of the Difco Yeast Nitrogen Base medium (without aminoacids) with 0.03 g/l KH$_2$PO$_4$, 1 g/l KCl, 10 g/l L-asparagine instead of (NH$_4$)$_2$SO$_4$, 2% glucose and 1 g/l L-histidine. The medium is inoculated to a starting OD$_{600}$ of 0.03. The cells are grown in a 500 ml flask at 30° C. for 24 hours (OD$_{600nm}$=1.8 for low P$_i$ medium, OD$_{600nm}$=3.0 for high P$_i$ medium).

c) Determination of eglin C titers

When the cells have reached a cell density (OD) as given above, the cells are harvested, centrifuged and disrupted by glass beads. The mixtures are assayed for eglin activity by measuring the inhibition of human leukocyte elastase according to the method of U. Seemueller et al. [Hoppe-Seyler's Z. Physiol. Chem. 358, 1105 (1977)]. The following activities are obtained:

| extract of S. cerevisiae | eglin C activity (mg/1/OD of culture) | |
|---|---|---|
| | induced (low P$_i$) | not induced (high P$_i$) |
| pJDB207/PAPEL-EGL (UAS1) | 14 | 0.7 |
| pJDB207/PAPFL-EGL (UAS1) | 17 | 0.7 |
| pJDB207/PAPEL-EGL (UAS1 + UAS2) | 14 | 1 |
| pJDB207/PAPFL-EGL (UAS1 + UAS2) | 11 | 0.7 |

EXAMPLE 5

Expression of Desulphatohirudin Under the Control of a PHO5-GAPDH Hybrid Promoter I. Adjustment of the nucleotide sequence at the 5' end of the desulphatohirudin HV1 gene The nucleotide sequence coding for desulphatohirudin (see European Patent Application No. 168,342) starts with GTT which stands for the NH$_2$-terminal valine in the final gene product. For convenient subcloning and expression in E. coli the coding sequence has been extended at the 5' end by eight nucleotides including an EcoRI restriction site and an ATG initiation codon. For the exact in frame fusion of the hirudin coding sequence to the sequence coding for the PHO5 signal peptide these additional nucleotides have to be removed. This is achieved by converting the EcoRI restricton site to a flush end site, adding a synthetic oligonucleotide containing a HgaI recognition site in such a position that subsequent cleavage with HgaI occurs immediately upstream of the GTT codon.

Introduction of a HgaI restriction site in front of 'the desulphatohirudin gene (see FIG. 7)

8 μg of plasmid pML310 (see EP 168,342) are digested to completion with restriction endonuclease EcoRI. The DNA (pML310/EcoRI) is extracted with phenol/chloroform and precipitated with ethanol. 5' overhanging ends are removed by nuclease S$_1$. 4 μg of pML310/EcoRI DNA are digested in 100 μl of 250 mM NaCl, 1 mM ZnSO$_4$, 30 mM sodium acetate pH 4.6 with 20 U/ml of nuclease S$_1$ (Sigma) for 45 min at 37° C.

The DNA is extracted with phenol/chloroform and precipitated by ethanol. The DNA (pML310/EcoRI/S$_1$) is resuspended in 100 μl of 50 mM Tris.HCl pH 8.0 and incubated with 2 units of calf intestine alkaline phosphatase (CIAP, Boehringer) for one hour at 37° C. The enzyme is inactivated at 65° C. for 1.5 hour.

The NaCl concentration in the incubation mixture is adjusted to 150 mM. The dephosphorylated DNA (pML310/EcoRI/S$_1$/CIAP) is purified by adsorption to a DE52 (Whatman) ion exchange column in a low salt buffer (150 mM NaCl, 10 mM Tris.HCl pH 8.0, 1 mM EDTA) and then eluted with a high salt buffer solution (1.5 M NaCl, 10 mM Tris.HCl pH 8.0, 1 mM EDTA). The DNA is precipitated with ethanol and resuspended in H$_2$O at a concentration of 0.8 mg/ml.

An oligonucleotide of the formula

5'-AGCGTCGACGCT-3' is synthesized by the phosphotriester method [Itakura et al., J. Am. Chem. Soc. 103, 706 (1981)]. The sequence of the oligonucleotide is self-complementary containing the recognition site —GACGC— for restriction endonuclease HgaI. Annealing of two single strands leads to a double-stranded DNA linker of 12 base pairs.

1.2 μg of the synthetic single-stranded oligodeoxynucleotide are phosphorylated in 10 μl of 60 mM Tris.HCl pH 7.5, 10 mM MgCl$_2$, 5 mM DTT, 30 μCi of [ε-$^{32}$P] ATP (3000 Ci.mmol$^{-1}$, Amersham) and 6 units of T$_4$ polynucleotide kinase (Boehringer) for 30 min at 37° C., followed by a 15 min chase at 37° C. in the presence of 0.5 mMATP. The mixture is further incubated for 10 min at 75° C. to inactivate the enzyme and is then allowed to cool to room temperature for annealing.

0.6 μg (170 pmoles) of the $^{32}$P-labelled linker DNA are mixed with 2.4 μg (1.75 pmol ends) of pML310/EcoRI/S$_1$/CIAP and ligated in 20 of 60 mM Tris.HCl pH 7.5, 10 mM MgCl$_2$, 5 mM DTT, 3.5 mMATP, 800 units of T$_4$ DNA ligase (Biolabs) for 20 hours at 15° C. The ligase is inactivated at 85° C. for 10 min and the excess of linker molecules is removed by precipitation of the DNA in the presence of 10 mM EDTA pH 7.5, 300 mM sodium acetate pH 6.0 and 0.54 volumes of isopropanol. After 30 min at room temperature the DNA is pelleted, resuspended in 45 μl of ligation mixture (specified above) and ligated for 6 hours at 15° C. to form circular DNA.

Aliquots of 1 μl and 3 μl of the ligation mixture are added to 100 μl of calcium-treated, transformation competent E. coli HB101 cells [prepared according to the method of D. Hanahan, J. Biol. Chem. 166, 557 (1983)]. The cells are left on ice for 30 min, then incubated for 3 min at 42° C., cooled on ice for 2 min and then incubated for one hour at 37° C. in 400 μl of SOC Medium. The cells are concentrated in 100 μl each and plated on LB agar plates containing 50 μg/ml of ampicillin.

12 transformed, amp$^R$ colonies are grown individually in LB medium containing 100 μg/ml of ampicillin. Plasmid DNA is prepared according to the method of D. S. Holmes et al. [Anal. Biochem. 114, 193 (1981)]. The presence of the synthetic oligonucleotide linker is confirmed by DNA sequencing using a single stranded DNA fragment as primer which hybridizes to the coding strand of hirudin. One clone which contains the linker DNA at the correct position in front of the hirudin gene is referred to as pML310L.

II. Fusion of the PHO5 signal sequence and the desulphatohirudin structural gene a) Isolation of the 0.2 kb desulphatohirudin fragment (see FIG. 7)

12 μg of plasmid pML310L are digested to completion with restriction endonucleases BamHI and PvuI. After extraction of the DNA by phenol/chloroform and ethanol precipitation the two restriction fragments are separated on a 1.2% agarose gel in tris-borate-EDTA buffer pH 8.3. The ethidiumbromide stained 0.84 kb PvuI-BamHI fragment is isolated in a gel slice. The DNA is electroeluted in a dialysis bag filled with 3 ml of 0.2×TBE buffer. The closed bag is submersed in TBE buffer pH 8.3 (90 mM Tris-base, 90 mM boric acid, 2.5 mM EDTA). After 30 min at 100 mA the polarity of the current is reversed for 45 sec. to repell the DNA from the dialysis membrane. The buffer surrounding the gel slice in the dialysis bag is recovered, adjusted to 150 mM NaCl and passed through a DE52 (Whatman) ion exchange column. The DNA is eluted with a high salt buffer (1.5 M NaCl, 10 mM Tris.HCl pH 8.0, 1 mM EDTA), precipitated with ethanol and redissolved in H$_2$O at a concentration of 0.1 mg/ml.

The 0.84 kb PvuI-BamHI fragment of pML310L is further digested with restriction endonuclease HgaI. This digest generates a 198 bp HgaI-BamHI fragment which contains the complete coding sequence for mature desulphatohirudin. Additional AluI digestion does not touch the 198 bp HgaI-BamHI fragment but eliminates another HgaI fragment of similar size.

The 0.2 kb HgaI-BamHI fragment is separated from other fragments on a 1.5% agarose gel in TBE buffer and is isolated by electroelution (as described above). The DNA is purified by DE52 ion exchange chromatography and ethanol precipitation. The DNA is resuspended in H$_2$O at a concentration of 30 µg/ml (0.2 pmoles/µl).

b) Isolation of the PHO5 promoter region with part of the PHO5 signal sequence (see FIG. 8)

Plasmid p31/PHOS-TPA18 (see European Patent Application No. 143,081) has the PHO5 promoter and the PHO5 signal sequence fused in frame to a foreign structural gene (t-PA). A 584 bp BamHI-BalI fragment contains the PHO5 promoter and all of the PHO5 signal sequence but eight nucleotides at the 3' end.

8 µg of p31/PHO5-TPA18 DNA are digested with restriction endonuclease BalI (16 hours at 37° C.). The DNA is purified by phenol/chloroform extraction and ethanol precipitation. The DNA is resuspended in H$_2$O at a concentration of 0.7 mg/ml.

The correct junction between the PHO5 signal sequence and the coding region for desulphatohirudin is provided by a synthetic linker of the formula (1) 5'-CCAATGCA-3'
(2) 3'-GGTTACGTCAACA-5'

Eight nucleotides at the 5' end of the linker (5'-CCAATGCA) represent part of the PHO5 signal sequence from the BalI site to the processing site. The 5' overhanging five nucleotides of oligonucleotide (2) fit into the HgaI cleavage site at the 5' end of the desulphatohirudin coding sequence.

The individual single stranded oligonucleotides (1) and (2) are synthesized by the phosphotriester method (Itakura et al., supra). 1.1 µg and 1.8 µg of oligonucleotides (1) and (2), respectively, are individually phosphorylated at their 5' ends, mixed in equimolar amounts and annealed as described in example 5I.

1.3 µg (200 pmoles) of the phosphorylated, double stranded linker DNA is ligated to 7 Bg (1.8 pmoles) of BalI cleaved p31/PHO5-TPA18 in 40 µl of 60 mM Tris.HCl pH 7.5, 10 mM MgCl$_2$, 3.5 mMATP, 5 mM DTT and 1400 units of T$_4$ DNA ligase (Biolabs) at 15° C. for 16 hours. The ligase is inactivated for 10 min at 85° C. The excess of linkers is removed by precipitation of the DNA in the presence of 10 mM EDTA, 300 mM sodium acetate pH 6.0 and 0.54 volumes of isopropanol. The DNA is resuspended and further digested with restriction endonuclease BamHI. After extraction of the DNA by phenol/chloroform and ethanol precipitation the two restriction fragments are separated on a 1.2% agarose gel in tris-borate-EDTA buffer pH 8.3. The 0.6 kb fragment is isolated from the gel. The DNA is electroeluted and further purified by DE52 ion exchange chromatography and ethanol precipitation. The 0.6 kb BamHI-HgaI DNA fragment is resuspended in H$_2$O at a concentration of 40 µg/ml.

c) Isolation of a pJDB207 yeast vector fragment (see FIG. 8)

9 µg of plasmid pJDB207R/PHOS-TPA(12-2) DNA (see European Patent Application No. 143,081) are digested with restriction endonuclease BamHI. Upon complete digestion, the DNA is extracted by phenol/chloroform and ethanol precipitated. The DNA is resuspended in 50 mM Tris.HCl pH 8.0 at a concentration of 0.1 mg/ml and digested with 7 units of calf intestine alkaline phosphatase for one hour at 37° C. The phosphatase is inactivated for 1.5 hours at 65° C. and the DNA is purified by DE52 ion exchange chromatography (see example 5I) and ethanol precipitation. The 6.8 kb large BamHI fragment is separated on a 1.2% agarose gel in tris-borate-EDTA buffer pH 8.3. The DNA is electroeluted and purified by DE52 ion exchange chromatography and ethanol precipitation. The DNA is dissolved in H$_2$O at a concentration of 0.4 mg/ml (0.1 pmoles/µl).

d) Ligation of the PHO5 promoter fragment and the desulphatohirudin structural gene to the pJDB207 yeast vector fragment (see FIG. 8)

The pJDB207 yeast vector, the PHO5 promoter fragment with the PHO5 signal sequence and the desulphatohirudin structural gene are all isolated as DNA fragments (see example 5II a–c) which are ligated to form an expression plasmid. 0.3 pmoles of the 0.6 kb BamHI-HgaI fragment of p31/PHOS-TPA18 and 0.3 pmoles of the 0.2 kb HgaI-BamHI fragment of pML310L are ligated to 0.1 pmoles of a 6.8 kb BamHI fragment of pJDB207R/PHO5-TPA (12-2) in 10 µl of 60 mM Tris.HCl pH 7.5, 10 mM MgCl$_2$, 5 mM DTT, 1 mMATP and 400 units of T$_4$ DNA ligase for 20 hours at 15° C.

A one µl aliquot of the ligation mixture is added to 100 µl of transformation competent E. coli HB101 cells prepared according to Hanahan (supra). The transformation protocol is also adopted from this publication. The cells are plated on LB agar plates containing 50 µg/ml of ampicillin.

24 amp$^R$ colonies are grown individually in LB medium with 100 µg/ml of ampicillin. Plasmid DNA is analysed for size and orientation of the insert by cleavage with restriction endonuclease PstI. A single clone with the correct orientation of the insert is referred to as pJDB207/PHO5-HIR.

III) Preparation of plasmid pJDB207/PHOS(Eco)-HIR (see FIG. 9)

For convenient joining of the UAS(PHO5)-GAPDH hybrid promoter elements to the coding region of desulphatohirudin including the PHO5 signal sequence (as in plasmid pJDB207/PHO5-HIR) an EcoRI restriction site is introduced in the 5' nontanslated region between the mRNA start sites and the ATG of the coding region.

15 µg of plasmid pJDB207/PHO-HIR are digested with restriction endonuclease DraI (Boehringer). The resulting 4 fragments are separated on a 0.8% agarose gel in Tris-borate-EDTA buffer pH 8.3. The 4.2 kb DNA fragment is recovered from the gel, electroeluted and precipitated by ethanol. The DNA is resuspended in H$_2$O at a concentration of 0.6 mg/ml.

Two synthetic oligonucleotides of the formula

5'-AATTCGATTACCAATGTTT-3'

-continued

3'- GCTAATGGTTACAAA-5'

(2.3 μg and 2.9 μg, respectively) are each kinased in 20 μl of 60 mM Tris pH 7.5, 10 mM MgCl₂, 5 mM DTT, 0.5 mMATP and 20 U of T4 polynucleotide kinase (Boehringer). After 45 min at 37° C. both reaction mixtures are combined, heated for 10 min at 75° C. and allowed to cool to room temperature. The annealed oligonucleotide linker is stored at −20° C.

6.5 μg (2.3 pmoles) of the 4.2 kb DraI DNA fragment are incubated for 16 h at 15° C. with a 70 fold excess of the kinased and annealed oligonucleotide linker in 50 μl of 60 mM Tris pH 7.5, 10 mM MgCl₂, 5 mM DTT, 3.5 mM ATP and 800 U of T4 DNA ligase (Biolabs). After inactivation of the T4 DNA ligase for 10 min at 85° C. the excess linkers are removed by precipitation of the DNA in the presence of 10 mM EDTA, 300 mM sodium-acetate pH 6.0 and 0.54 volumes of isopropanol. The DNA is digested with EcoRI and HindIII. The resulting fragments are separated on a 1% agarose gel in Trisborate-EDTA buffer pH 8.3. The 643 bp fragment is recovered from the gel by electroelution and ethanol precipitation. The DNA is resuspended at a concentration of 0.1 pmoles/μl. The EcoRI-HindIII fragment contains the PHO5 signal sequence, the coding sequence of desulphatohirudin and the PHO5 transcription terminator.

The 534 bp PHO5 promoter fragment is isolated from plasmid p31/R (European Patent Application No. 100,561).

Ten μg of p31/R are digested with restricton endonucleases EcoRI and BamHI. The resulting 3 fragments are separated on a 0.6% low melting agarose gel in Tris-borate-EDTA buffer pH 8.3. A 534 bp BamHI-EcoRI fragment is isolated which contains the PHO5 promoter including the mRNA start sites.

The vector fragment is isolated from plasmid pJDB207/PHO5-HIR. 6 μg of this plasmid are digested with BamHI and HindIII. The large 6.5 kb BamHI-HindIII fragment is separated from the small fragment on a 0.6% low melting agarose gel in Tris-borate-EDTA buffer pH 8.3.

Three DNA fragments described above with the appropriate sticky ends are ligated in the following reaction: 0.2 pmoles (70 ng) of the 534 bp BamHI-EcoRI PHO5 promoter fragment, 0.2 pmoles (85 ng) of the 643 bp EcoRI-HindIII fragment (hirudin coding sequence) and 0.1 pmole (0.4 μg) of the 6.5 kb BamHI-HindIII vector fragment are ligated in 10 μl of 60 mM Tris pH 7.5, 10 mM MgCl₂, 5 mM DTT, 1 mM ATP and 400 U of T4 DNA ligase for 6 h at 15° C. A one μl aliquot of the ligation mixture is added to 100 μl of calcium treated, transformation competent *E. coli* HB 101 cells.

12 transformed, amp$^R$ colonies are grown individually in LB medium containing 100 μg/ml of ampicillin. Plasmid DNA is prepared according to the method of Holmes et al. [Anal. Biochem. 114 (1981) 193] and is analysed by EcoRI and BamHI restriction digests. One clone with the expected restriction fragments is isolated and referred to as pJDB207/PHO5(Eco)-HIR.

IV) Ligation of the UAS1(PHO5)-GAPDH hybrid promoters to the protein coding region of desulphatohirudin 15 μg of plasmid pJDB207/PHO5(Eco)-HIR are digested with EcoRI and HindIII. The DNA fragments are separated on a 1% agarose gel in Tris-borate-EDTA buffer pH 8.3. The 643 bp fragment is isolated from the gel, electroeluted and precipitated with ethanol. The DNA is resuspended in H₂O at a concentration of 0.1 pmoles/μl.

6 μg of plasmid pJDB207/PHO5-HIR are digested to completion with restriction endonucleases HindIII and SalI. The large 6.3 kb fragment (vector part) is isolated by soft agarose gel electrophoresis, phenol extraction and ethanol precipitation. The vector DNA fragment is resuspended in H₂O at a concentration of 0.05 pmoles/μl.

10 μg of plasmid pGAPDH-EL (see Example 3dI) are digested with BglII and EcoRI. The 266 bp BglII-EcoRI fragment is separated on a 1.2% agarose gel in Tris-borate-EDTA buffer pH 8.3, electroeluted from the gel and precipitated with ethanol. The DNA is resuspended in H₂O at a concentration of 0.3 pmoles/μl.

0.3 pmoles of the 548 bp SalI-BglII fragment comprising UAS1(PHO5) (Example 3dII), 0.3 pmoles of the 266 bp BglII-EcoRI fragment of pGAPDH-EL, 0.3 pmoles of the 643 bp EcoRI-HindIII fragment of pJDB207/PHO5(Eco)-HIR and 0.12 pmoles of the 6.3 kb SalI-HindIII vector fragment are ligated in 20 μl of 60 mM Tris pH 7.5, 10 mM MgCl₂, 5 mM DTT, 1 mM ATP and 400 U of T4 DNA ligase (Biolabs) for 6 h at 15° C. Aliquots of 1 μl and 3 μl of the ligation mixture are added to 100 μl of calcium treated *E. coli* HB101 cells. Plasmid isolation from amp$^R$ colonies and restriction analysis with SalI, BglII, EcoRI and HindIII is performed as described above (see Example 3dIII). One positive clone is selected and referred to as pJDB207/PAPEL-HIR(UAS1). An analogous construction is done with the 201 bp BglII-EcoRI fragment isolated from pGAPDH-FL. One selected plasmid is called pJDB207/PAPFL-HIR(UAS1).

V) Ligation of the UAS1(PHO5)-UAS2(PHO5)-GAPDH hybrid promoters to the protein coding region of desulphatohirudin p 3 μg each of plasmids pJDB207/PAPEL-HIR(UAS1) and pJDB207/PAPFL-HIR(UAS1) are digested with BglII. After phenol extraction and ethanol precipitation the 3' recessed ends of the DNA are filled in a reaction with *E. coli* DNA polymerase (Klenow fragment; Bethesda Research Laboratories) according to Maniatis et al. (supra). The enzyme is inactivated at 70° C. for 10 min. The DNAs are further digested with SalI and the large 7.2 kb fragments are isolated by soft agarose gel electrophoresis, phenol extraction and ethanol precipitation. Each fragment is resuspended in H₂O at a concentration of 0.05 pmoles/μl. The fragments contain the hirudin coding region, most of the vector sequences and either of two different GAPDH promoter elements isolated from pGAPDH-EL or pGAPDH-FL.

Plasmid p31/Y (European Patent Application No. 100,561) is digested with BstEII, incubated with *E. coli* DNA polymerase (Klenow fragment) as described above and cleaved with SalI. The 649 bp fragment is separated on a soft agarose gel and recovered by phenol extraction and ethanol precipitation.

0.3 pmoles of the 649 bp fragment of p31/Y comprising the UAS1-UAS2(PHO5) promoter element and 0.15 pmoles of either of the 7.2 kb fragments are ligated and transformed into *E. coli* HB101 as described above. Plasmids are prepared from amp$^R$ colonies and analysed by restricton digests. Single clones are selected and their plasmid DNAs are referred to as pJDB207/PA- PEL-HIR(UAS1+UAS2) and pJDB207/PAPFL-HIR(UAS1+UAS2).

EXAMPLE 6
A 31 bp DNA Sequence is Sufficient to Act as a Phosphate Control Element A 31 bp sequence from the upstream region of the PHO5 promoter (position −381 to −351), defined by the two flanking deletions Δ10 and Δ13 (see Example 1f), could potentially contain a regulatory signal. This can be tested by chemically synthesizing two complementary oligonucleotides of the following structure:

```
5'-AATTCGAAATATATATTAAATTAGCACGTTTTCGCAG-3'
3'-    GCTTTATATATAATTTAATCGTGCAAAAGCGTCTTAA-5'
```

This sequence contains the 31 bp sequence flanked by EcoRI restriction sites. The EcoRI sites allow easy polymerisation of the sequence to form multimers.

a) Cloning of the 31 bp element into vector LT98

50 pmoles of the two synthetic oligonucleotides are each kinased in 20 ml of 60 mM Tris pH 7.5, 10 mM MgCl₂, 5 mM DTT, 0.5 mM ATP and 20 U of T4 polynucleotide kinase (Boehringer). After 45 min at 37° C. both reaction mixtures are combined, heated for 10 min at 75° C. and allowed to cool to room temperature. The annealed oligonucleotides are stored at −20° C. 7.5 pmoles of the kinased and annealed oligonucleotides are ligated for 30 min as described above (Example 5III) in a total volume of 15 μl. Then, 5 μl of EcoRI cut LT98 vector DNA [Dixon et al., Gene 25, 189 (1983)] is added (0.075 pmole) and the incubation is continued for a total of 6 hours. After transformation into E. coli HB101 plasmids are isolated and analyzed by digestion with BamHI. This analysis provides data about the total length of the insert and allows to estimate the number of EcoRI fragments cloned. Individual plasmids with 1,2,3,4 or 5 EcoRI fragments are selected and DNA sequencing (Sanger method) indicates that the multiple 31 bp elements are cloned in head to tail orientation.

b) Cloning into pJDB207

The 31 bp oligomers are tested for their promoter control function by inserting them upstream of the F element of the GAPDH promoter. Plasmid pJDB207/PAPFL-EGL(UAS1) is shortened to produce a plasmid which has the UAS1 element deleted: The plasmid is digested with SalI and BglII, gel purified and the large vector fragment is isolated. In an independent reaction mix the same plasmid is digested with BamHI. The recessed 3' ends are filled in with Klenow DNA polymerase using all four dNTP's. The blunt ended sites are extended with phosphorylated BglII linkers (CAGATCTG, Biolabs), and after digestion with SalI and BglII a DNA fragment having an approximate length of 400 bp is isolated by gel purification. The large vector fragment is ligated with the approximate 400 bp SalI-BglII fragment using T4 DNA ligase. After E. coli HB101 transformation and plasmid isolation a plasmid is obtained without a PHO5 UAS, This plasmid is called pJDB207/GAPFL-EGL. This plasmid is digested with BglII and serves as a vector for cloning the 31 bp oligomers. LT98 containing 1,2,3,4 or 5 oligonucleotide inserts is digested with BamHI. The various size fragments are isolated by gel purification and independently ligated to the BglII cut pJDB207/GAPFL-EGL. The ligation mix is digested with BglII to remove unwanted religated vector without DNA insert and then used to transforme E. coli HB101. The plasmids obtained are analyzed by restriction analysis with SalI and DraI (a site within the GAPDH promoter part). After transformation of yeast strain GRF18 eglin C titers are determined as described in Example 4c. The following specific activities are measured after 46 hours of fermentation:

| clone pJDB207/ | number of 31 bp inserts | orientation* | eglin C titer (mg/l/OD) low $P_i$ | high $P_i$ |
|---|---|---|---|---|
| PAPFLI(+)-EGL | 1 | → | 9.2 | 5.2 |
| PAPFLI(−)-EGL | 1 | ← | 10.2 | 2.1 |
| PAPFLII(+)-EGL | 2 | → | 10.2 | 3.5 |
| PAPFLIII(−)-EGL | 3 | ← | 11.2 | 1.4 |
| PAPFLIV(+)-EGL | 4 | → | 10.7 | 1.5 |
| PAPFLV(−)-EGL | 5 | ← | 12.6 | 1.4 |

*→ same orientation as in PHO5 promoter
← reversed orientation as in PHO5 promoter

EXAMPLE 7
Expression of Insulin Like Growth Factor 1 (IGF-1) from a PAPFL Promoter Plasmid pAB113-IGF-1 as described in European Patent Application No. 123,228 is digested with PstI. Two synthetic oligonucleotides (50 pmol) each of the formula

```
AATTCATGAGATTTCCTTCAATTTTTACTGCA
    GTACTCTAAAGGAAGTTAAAAATG
``` are each kinased and annealed as described above. The annealed double stranded adapter is ligated to the PstI cut plasmid, digested with EcoRi and BamHI and the about 800 bp EcoRI-BamHI fragment is isolated by gel purification. Plasmid pJDB207/PAPFL-EGL(UAS1) is digested with SalI and EcoRI and the about 700 bp fragment is isolated by gel purification. In a triple ligation 0.5 μg of plasmid pCl/1 (European Patent Application No. 123,228; digested with BamHI and SalI, vector gel purified) is ligated with 100 ng of each of the two smaller gene and promoter parts, respectively. After E. coli transformation the plasmids are analyzed by EcoRI, BamHI and SalI digestion. Transformation of yeast strain AB103 [deposited at ATCC under No. 20,673; abortion of pYIGF-1-10/1 by growing yeast cells in a complex medium overnight and testing individual colonies for the presence of the IGF-1 μlasmid by colony hybridisation as described by Hinnen et al. [Proc. Natl. Acad. Sci. USA 75, 1929 (1978)]] gives transformants which produce IGF-1 only under induced (low $P_i$) conditions (1 mg/l) as determined with conventional competitive radioimmunoassay employing radiolabeled IGF-1 (Anderson et al., in: Somatomedins/Insulin-Like Growth Factors, Spencer, E. M., ed., Walter de Gruyter, Berlin). The clones are designated pCl/1/PAPFL-IGF-1(UAS1).

EXAMPLE 8

Expression of Tissue Plasminogen Activator (t-PA) Under the Control of a PHO5-GAPDH Hybrid Promoter (see FIG. 10)

12 μg of plasmid pJDB207/PHO5-TPA18 (European Patent Application No. 143,081) are digested to completion with restriction endonucleases SalI and HindIII. The resulting two DNA fragments are separated on a 0.8% agarose gel in Tris-borate-EDTA buffer pH 8.3. The small 2.6 kb SalI-HindIII fragment is isolated by electroelution, phenol extraction and ethanol precipitation. The DNA is further digested with BalI. The 1.8 kb fragment with part of the PHO5 signal sequence, the coding sequence of t-PA and the PHO5 terminator is isolated and purified as above and is resuspended in H$_2$O at a concentration of 0.1 pmoles/μl.

The hybrid promoter fragment is isolated from plasmid pJDB207/PAPFL-HIR(UAS1 + UAS2) (see Example 5V). 12 μg of plasmid DNA are digested with SalI and HindIII. The resulting 1.5 kb fragment is further digested with BalI. A 920 bp fragment comprising the hybrid promoter and part of the PHO5 signal sequence is isolated on a 1.5% agarose gel. The DNA is electroeluted, phenol extracted, precipitated with ethanol and resuspended in H$_2$O at a concentration of 0.1 pmoles/μl.

0.2 pmoles of the 920 bp SalI-BalI fragment, 0.2 pmoles of the 1.8 kb BalI-HindIII fragment and 0.1 pmoles of the SalI, HindIII cleaved vector pJDB207 are ligated for 16 h at 15° C. in a total volume of 10 μl. A one μl aliquot of the ligation mixture is added to 100 μl of calcium treated, transformation competent *E. coli* HB101 cells.

12 transformed amp$^R$ colonies are grown individually in LB medium containing 100 μg/ml of ampicillin. Plasmid DNA is prepared according to the method of Holmes et al. [Anal. Biochem. 114, 193 (1981)] and is analysed by PstI and BamHI/EcoRI restriction digests. One clone with the expected restriction fragments is isolated and referred to as pJDB207/PAPFL-TPA(UAS1+UAS2).

An analogous construction is done for the UAS1(-PHO5) element: A 820 bp SalI-BalI fragment of pJDB207/PAPFL-HIR(UAS1) (Example 5IV) is isolated and ligated to the 1.8 kb BalI-HindIII fragment and the SalI, HindIII cleaved vector. The resulting plasmid is referred to as pJDB207/PAPFL-TPA(UAS1).

Analogous constructions are done with corresponding fragments isolated from pJDB207/PAPEL-HIR(UAS1) or pJDB207/PAPEL-HIR(UAS1+UAS2) (Example 5). Resulting plasmids are referred to as pJDB207/PAPEL-TPA(UAS1) and pJDB207/PAPEL-TPA(UAS1+UAS2).

EXAMPLE 9

Expression of Polypeptides Under the Control of PHO5-GAPDH Hybrid Promoters a) Transformation of Saccharomyces cerevisiae GRF18:

*Saccharomyces cerevisiae* strain GRF18 (α, his3-11, his3-15, leu2-3, leu2-112, can$^R$) is transformed with the plasmids pJDB207/PAPEL-HIR(UAS1)
pJDB207/PAPFL-HIR(UAS1)
pJDB207/PAPEL-HIR(UAS1+UAS2)
pJDB207/PAPFL-HIR(UAS1+UAS2)
pJDB207/PAPFLI(+)-EGL
pJDB207/PAPFLI(−)-EGL
pJDB207/PAPFLII(+)-EGL
pJDB207/PAPFLIII(−)-EGL
pJDB207/PAPFLIV(+)-EGL
pJDB207/PAPFLV(−)-EGL
pJDB207/PAPEL-TPA(UAS1)
pJDB207/PAPFL-TPA(UAS1)
pJDB207/PAPEL-TPA(UAS1+UAS2)
pJDB207/PAPFL-TPA(UAS1+UAS2)
pCl/1/PAPFL-IGF-1(UAS1)

using the transformation protocol described by Hinnen et al. [Proc. Natl. Acad. Sci. USA 7-5, 1929 (1978)]. Transformed yeast cells are selected on yeast minimal media plates deficient in leucine. Single transformed yeast colonies are isolated and referred to as

*Saccharomyces cerevisiae* GRF18/pJDB207/PAPEL-HIR(UAS1)
*Saccharomyces cerevisiae* GRF18/pJDB207/PAPFL-HIR(UAS1)
*Saccharomyces cerevisiae* GRF18/pJDB207/PAPEL-HIR(UAS1+UAS2)
*Saccharomyces cerevisiae* GRF18/pJDB207/PAPFL-HIR(UAS1+UAS2)
*Saccharomyces cerevisiae* GRF18/pJDB207/PAPFL-I(+)-EGL
*Saccharomyces cerevisiae* GRF18/pJDB207/PAPFLI(−)-EGL
*Saccharomyces cerevisiae* GRF18/pJDB207/PAPFLII(+)-EGL
*Saccharomyces cerevisiae* GRF18/pJDB207/PAPFLIII(−)-EGL
*Saccharomyces cerevisiae* GRF18/pJDB207/PAPFLIV(+)-EGL
*Saccharomyces cerevisiae* GRF18/pJDB207/PAPFLV(−)-EGL
*Saccharomyces cerevisiae* GRF18/pJDB207/PAPEL-TPA(UAS1)
*Saccharomyces cerevisiae* GRF18/pJDB207/PAPFL-TPA(UAS1)
*Saccharomyces cerevisiae* GRF18/pJDB207/PAPEL-TPA(UAS1+UAS2)
*Saccharomyces cerevisiae* GRF18/pJDB207/PAPFL-TPA(UAS1+UAS2)
*Saccharomyces cerevisiae* GRF18/pCl/1/PAPFL-IGF-1(UAS1)

b) Fermentation of the transformants

Cells of the *S. cerevisiae* GRF18 transformants are each grown in 10 ml of yeast minimal medium (Difco Yeast Nitrogen Base without aminoacids to which 2% glucose and 20 mg/l L-histidine are added) in a 50 ml Erlenmeyer flask with shaking at 30° C. for 24 hours to a density of 3×10$^7$ cells/mi. The cells are washed in 0.9% NaCl and used to inoculate 50 ml of a low P$_i$ minimal medium prepared according to the recipe of the Difco Yeast Nitrogen Base medium (without amino acids), but containing 0.03 g/l KH$_2$PO$_4$, 1 g/l KCl and 10 g/l L-asparagine instead of (NH$_4$)$_2$SO$_4$, 2% glucose and 1 g/l L-histidine. The cultures are inoculated up to a cell density of 4×10$^6$ cells/ml and agitated at 30° C. for up to 42 hours at 200 revs/min.

c) Titers of expressed gene products

Yeast secretes desulphatohirudin compounds into the culture broth. After fermentation for 22 h a 10 ml sample is taken from the culture medium and is enriched for proteins by desalting and concentration on a Bond Elut C-18 column (1 ml, Analytichem International). The column is washed twice with 1.5 ml water-acetonitril (9:1)-0.1% trifluoroacetic acid. Desulphatohirudin compounds are eluted from the column with water-acetonitril-0.1% trifluoroacetic acid (6:4 v/v). 2 ml eluate are concentrated at a Speed Vac concentrator (Savant) to a final volume of 400 µl. Desulphatohirudin is identified by HPLC analysis, by comparison with authentic desulphatohirudin and by means of the thrombin inhibition assay [cf. M. U. Bergmeyer (ed.), Methods in Enzymatic Analysis, Vol. II, p. 314-316, Verlag Chemie, Weinheim (FRG) 1983].

The results are shown in Table 1.

TABLE 1

Secretion of desulphatohirudin into the culture broth by S. cerevisiae strain GRF18 transformed with different plasmids:

| plasmid | desulphatohirudin [mg/l culture broth/OD$_{600}$] |
| --- | --- |
| pJDB207/PAPEL-HIR (UAS1) | 2.0 |
| pJDB207/PAPFL-HIR (UAS1) | 2.2 |
| pJDB207/PAPFL-HIR (UAS1 + UAS2) | 3.0 |
| pJDB207/PAPEL-HIR (UAS1 + UAS2) | 2.8 |

Tissue plasminogen activator (t-PA) accumulates in the yeast cells. Cell extracts are prepared and the t-PA activity is determined as follows: Cells from 35 ml of low P. culture medium [B. Meyhack et al. EMBO-J. 1, 675 (1982)] at a cell density of $1-2 \times 10^7$/ml are collected by centrifugation in a Sorvall SS34 rotor for 10 min at 3000 rpm. The cells are washed in a buffer containing the salt components of the culture medium (i.e. without aminoacids, glucose, vitamins, trace elements). The cells are centrifuged at room temperature for 5 min at 3000 rpm. The sedimented cells are resuspended in a total volume of 4 ml of cold 66 mM sodium phosphate buffer pH 7.4 and 0.1% (v/v) Triton X-100. The cell suspension is transferred to a 30 ml Corex tube, 8 g of glass beads (0.4 mm in diameter) are added and the suspension is shaken on a Vortex Mixer (Scientific Instruments Inc., USA) at full speed for 4 min and then cooled in an ice bath. More than 90% of the cells are broken by this procedure. Cell debris and glass beads are sedimented by centrifugation for 10 min at 8000 rpm at 4° C. in a Sorvall Hβ-4 rotor. The supernatant is transferred to Eppendorf tubes, frozen in liquid nitrogen and stored at −60° C.

t-PA activity is determined according to the method of Rånby [Biochim. Biophys. Acta 704, 461 (1982)] with slight modifications. D-Val-Leu-Lys-pNA (Kabi S-2251) is used as substrate. The absorption at 405 nm is corrected for unspecific cleavage and related to an urokinase standard. The results are shown in Table 2.

TABLE 2 t-PA activity in S. cerevisiae strain GRF18 transformed with different plasmids:

| plasmid | t-PA activity [I.U./l yeast cell culture/OD$_{600}$] |
| --- | --- |
| PJDB207/PAPFL-TPA (UAS1) | 300 |
| PJDB207/PAPFL-TPA (UAS1 + UAS2) | 200 |

EXAMPLE 10

Isolation and Characteristion of IGF-1 from a Transformed Yeast Strain a) Isolation of IGF-1 from the culture medium:

Yeast strain pCl/1/PAPFL-IGF-1(UAS1) is cultivated for 60 h. 3 l culture broth is harvested and centrifuged as described in example 9. Analysis by reversed phase HPLC of 2 ml supernatant (1:10 conc.) yields a titer of 1 mg/l IGF-1. The supernatant is treated with 20 ml SP-Sephadex C-25 (Pharmacia) at pH 3.0 and stirred for 60 min at 4° C. The adsorbed IGF-1 is eluted from the washed resin by a sodium acetate buffer gradient (50 mM, pH 3.0 to pH 9.0) and further purified by two ion exchange steps: The first step is carried out on a CM-52 column (Whatman, 1.5 cm×8.5 cm, gradient, buffer A 20 mM NH$_4$OAc pH 4.0; buffer B 100 mM NH$_4$OAc pH 6.8). The second step is performed on a DE-53 anion exchange column (Whatman) (conditions: 1.5 cm×10.5 cm column, flow 1 ml/min, gradient, buffer A 20 mM NH$_4$OAc pH 9.0; buffer B 200 mM NH$_4$OAc pH 6.5). The final purification is carried out on a semipreparative RP-HPLC column. The active fraction elutes with retention time 21.3 min yielding 1.1 mg of 95% pure IGF-1.

Experimental conditions: Vydac 218 TP 510 RP-HPLC column, 10×250 mm; aliquot portions (200 µl concentrated 1:10) per separation; AUFS 0.5 at 220 nm; flow rate: 3 ml/min. Eluant: A: 0.1% trifluoroacetic acid, B: acetonitrile/water 8:2+0.07% trifluoroacetic acid, 3 min 35% B, then increase in the course of 30 min to 45% B. The resulting fractions are diluted 1:1 with water and lyophilised.

b) Characterization of IGF-1 from the fermentation of the strain pCl/1/PAPFL-IGF-1(UAS1)

According to RP-HPLC analysis IGF-1 isolated from the culture medium (cf. example 10a) is identical to authentic IGF-1 from serum.

Isoelectric point pI:8.6 (Isoelectric focussing, TCA precipitation of the protein).

Determination of the amino acid composition

Approximately 2.5 µg of the pure IGF-1 is hydrolyzed for 24 h with 6 N HCl at 110° C. and then analyzed as described by Chang et al. [DABS-Cl method; Methods in Enzymology 91, 41 (1983)]. The hydrolysate has the following composition:

| Amino acid | Hydrolysate | | Amino acid | Hydrolysate | |
| --- | --- | --- | --- | --- | --- |
| Asp | 5.7 | (5) | Ile | 0.7 | (1) |
| Thr | 3.2 | (3) | Leu | 5.9 | (6) |
| Ser | 5.2 | (5) | Tyr | 2.8 | (3) |
| Glu | 6.5 | (6) | Phe | 3.9 | (4) |
| Pro | 5.3 | (5) | His | — | — |
| Gly | 7.2 | (7) | Lys | 3.0 | (3) |
| Ala | 6.1 | (6) | Arg | 6.0 | (6) |
| Val | 2.7 | (3) | Met | 0.9 | (1) |
| Cystin | 2.2 | (3) | Total | | (70) |

Partial sequence analysis

70 µg (10 nmol) of the pure IGF-1 is subjected to a conventional sequence analysis according to Edman. The N-terminal PTH-amino acids are determined by means of RP-HPLC.

Results:

| Cycle | 1 | 5 | 10 |
|---|---|---|---|
| Amino acid | Gly—Pro—Glu—Thr—Leu—Cys*—Gly—Ala—Glu—Leu— | | |
| Cycle | 11 | 15 | 20 |
| Amino acid | Val—Asp—Ala—Leu—Gln—Phe—Val—Cys*—Gly—Asp— | | |
| Cycle | 21 | 25 | 30 |
| Amino acid | Arg—Gly—Phe—Tyr—Phe—Asn—Lys—Pro—Thr—Gly— | | |
| Cycle | 31 | 35 | 40 |
| Amino acid | Tyr—Gly—Ser—Ser—Ser—Arg—Arg—Ala—Pro—Gln— | | |
| Cycle | 41 | 45 | 50 |
| Amino acid | Thr—Gly—Ile—Val—Asp—Glu—n.d.—n.d.—Phe—Arg— | | | n.d.: not determined
*: Cys (6) and Cys (18) are determined separately by carboxymethylation with iodine acetamide.

The partial sequence from amino acid 1 to 50 is thus identical to the published primary sequence of authentic IGF-1.

C-terminal analysis

The pure IGF-1 is digested with carboxypeptidase Y and the released amino acids determined in the amino acid analyser (of. J. Y. Chang, R. Knedel, D. G. Braun, Blochem. J. 199, 547).

Results:

| amino acid | 70 |
|---|---|
| 5 min digestion: | —Ala |
| 120 min digestion: | Ser—Ala |

Apparent molecular weight

The IGF-1 (30 μg) is analysed on a SDS urea gel [SUDS gel; cf. Kyte et al., Anal. Blochem. 133, 515 (1983)]. A single band corresponding to an apparent molecular weight of 6000 to 7000 Daltons is observed.

Molecular weight determination by FAB-MS

The IGF-1 is subjected to fast atom bombardment positive ion mass spectrometry (FAB-MS). Instrument: ZAB-HF mass spectrometer from VG-Analytical Ltd., Manchester; matrix: thioglycerol; Xenon bombardment; ion energy 3 KeV; external calibration: $Cs_{30}J_{29}$ (molecular weight: 7667.4)

empirical formula: $C_{331}H_{518}N_{94}O_{101}S_7$
molecular weight (calculated): 7648.71
molecular weight (found): 7648.07

What is claimed is:

1. A yeast hybrid promoter including a 5' upstream promoter element comprising upstream activation site(s) of the yeast PHO5 gene and a 3' downstream promoter element of the yeast GAPDH gene starting at nucleotide −300 to −180 and ending at nucleotide −1 of the GAPDH gene.

2. A hybrid promoter according to claim 1 in which the 5' upstream promoter element is the 368 bp BamHI-BstEII fragment of the 5' region of the yeast PHO5 gene.

3. A hybrid promoter according to claim 1 in which the 5' upstream promoter element is the 268 bp BamHI-ClaI fragment of the 5' region of the yeast PHO5 gene.

4. A hybrid promoter according to claim 1 in which the 5' upstream promoter element is the 31 bp DNA of the formula

GAAATATATATTAAATTAGCACGTTTTC-GCA
CTTTATATATAATTTAATCGT-GCAAAAGCGT.

5. A hybrid promoter according to claim 1 in which the 5' upstream promoter element is the 100 bp ClaI-BstEII fragment of the 5' region of the yeast PHO5 gene.

6. A hybrid promoter according to claim 1 containing UAS1(PHO5) and UAS2(PHO5).

7. A hybrid promoter according to claim 1 containing UAS1(PHO5).

8. A hybrid promoter according to claim 1 containing UAS2(PHO5).

9. A hybrid promoter according to claim 1 in which the 3'downstream promoter element comprises nucleotides −199 to −1 of the yeast GAPDH gene.

10. A hybrid promoter according to claim 1 in which the 3' downstream promoter element comprises nucleotides −263 to −1 of the yeast GAPDH gene.

11. A hybrid promoter according to claim 1 which contains multiple upstream activation sequences UAS1.

12. A hybrid promoter according to claim 11 containing 2 to 4 upstream activation sequences UAS1.

13. A hybrid promoter according to claim 11 containing 2 upstream activation sequences UAS 1.

14. A hybrid promoter according to claim 11 containing 3 upstream activation sequences UAS1.

15. A hybrid promoter according to claim 11 containing 4 upstream activation sequences UAS 1.

16. The upstream activation sequence UAS1 (PHO5) contained in the BamHI-ClaI fragment between nucleotides −274 to −541 of the PHO5 gene according to claim 11.

17. The upstream activation sequence UAS1(PHO5) contained in the DNA of the formula

GAAATATATATTAAATTAGCACGTTTTCGCA
CTTTATATATAATTTAATCGTGCAAAAGCGT according to claim 11.

18. A yeast hybrid vector containing one or multiple DNA inserts each comprising a DNA segment coding for a polypeptide heterologous to yeast under the transcriptional control of a hybrid promoter consisting of a 5' upstream promoter element with UAS(s) of the yeast PHO5 gene and a 3' downstream promoter element of the yeast GAPDH gene starting at nucleotides −300 to −180 and ending at nucleotide −1 of the GAPDH gene.

19. A hybrid vector according to claim 18 in which the yeast hybrid promoter is directly linked by the way of an inserted ATG to the coding region of a mature polypeptide.

20. A hybrid vector according to claim 18 in which the polypeptide coding region codes for a polypspride having a signal sequence.

21. A hybrid vector according to claim 18 comprising as the 5' upstream promoter element the 368 bp BamHI- BstEII fragment of the 5' region of the yeast PHO5 gene and a 3' downstream promoter element comprising nucleotides −263 to −1 of the yeast GAPDH gene.

22. A yeast host transformed with a hybrid vector containing one or multiple DNA inserts each comprising a DNA segment coding for a polypeptide heterologous to yeast under the transcriptional control of a hybrid promoter consisting of a 5' upstream promoter element with UAS(s) of the yeast PHO5 gene and a 3' downstream promoter element of the yeast GAPDH gene starting at nucleotides −300 to −180 and ending at nucleotide −1 of the GAPDH gene.

23. A method for producing a polypspride heterologous to yeast characterized in that a yeast strain transformed with a hybrid vector containing one or multiple DNA inserts each comprising a DNA segment coding for a polypspride heterologous to yeast under the transcriptional control of a hybrid promoter consisting of a 5' upstream promoter element with UAS(s) of the yeast PHO5 gene and a 3' downstream promoter element of the yeast GAPDH gene starting at nucleotides −300 to −180 and ending at nucleotide −1 of the GAPDH gene is cultured and the expressed polypspride is isolated.

24. A method according to claim 23 in which the DNA sequence codes for a polypeptide of higher eukaryotic origin.

25. A method according to claim 23 in which the DNA sequence codes for a polypeptide selected from the group consisting of a human e-interferon, a human hybrid interferon, human t-PA, HBVsAg, desulphatohirudin, eglin C and insulin-like growth factor.

26. A method for the production of eglin C according to claim 23.

27. A method for the production of desulphatohirudin according to claim 23.

28. A method for the production of human t-PA according to claim 23.

29. A method for the production of insulin-like growth factor according to claim 23.

* * * * *